(12) United States Patent
Matsunaga et al.

(10) Patent No.: US 10,611,708 B2
(45) Date of Patent: Apr. 7, 2020

(54) METHOD FOR PRODUCING 1,2-DICHLORO-3,3,3-TRIFLUOROPROPENE

(71) Applicant: Central Glass Company, Limited, Ube-shi, Yamaguchi (JP)

(72) Inventors: Kei Matsunaga, Kawagoe (JP); Hideaki Imura, Fujimino (JP); Masatomi Kanai, Kawagoe (JP); Masahiko Tani, Kawagoe (JP); Naoto Takada, Saitama (JP); Kohei Sumida, Kawagoe (JP); Satoru Okamoto, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 16/094,228

(22) PCT Filed: Apr. 10, 2017

(86) PCT No.: PCT/JP2017/014648
§ 371 (c)(1),
(2) Date: Oct. 17, 2018

(87) PCT Pub. No.: WO2017/183501
PCT Pub. Date: Oct. 26, 2017

(65) Prior Publication Data
US 2019/0092711 A1 Mar. 28, 2019

(30) Foreign Application Priority Data

Apr. 19, 2016 (JP) .............................. 2016-083439
Mar. 24, 2017 (JP) .............................. 2017-058985

(51) Int. Cl.
| | | |
|---|---|---|
| C07C 17/25 | (2006.01) | |
| C07C 17/20 | (2006.01) | |
| C07C 17/38 | (2006.01) | |
| C07C 17/383 | (2006.01) | |
| B01J 27/12 | (2006.01) | |
| C07C 17/04 | (2006.01) | |
| B01J 27/08 | (2006.01) | |
| B01J 37/26 | (2006.01) | |
| B01J 27/125 | (2006.01) | |
| B01J 27/132 | (2006.01) | |
| C07C 17/35 | (2006.01) | |

(52) U.S. Cl.
CPC ............ *C07C 17/206* (2013.01); *B01J 27/08* (2013.01); *B01J 27/12* (2013.01); *B01J 27/125* (2013.01); *B01J 27/132* (2013.01); *B01J 37/26* (2013.01); *C07C 17/04* (2013.01); *C07C 17/25* (2013.01); *C07C 17/35* (2013.01); *C07C 17/38* (2013.01); *C07C 17/383* (2013.01)

(58) Field of Classification Search
CPC ............................... C07C 17/25; C07C 17/206
See application file for complete search history.

(56) References Cited

U.S. PATENT DOCUMENTS

| | | |
|---|---|---|
| 6,759,381 B1 | 7/2004 | Johnson et al. |
| 7,094,936 B1 | 8/2006 | Owens et al. |
| 8,987,532 B2 | 3/2015 | Okamoto et al. |
| 2012/0053374 A1 | 3/2012 | Fukuju et al. |
| 2013/0041190 A1* | 2/2013 | Pigamo ................. C01B 7/0712 570/156 |

FOREIGN PATENT DOCUMENTS

| | | |
|---|---|---|
| CN | 103508842 A | 1/2014 |
| CN | 103508844 A | 1/2014 |
| CN | 105753637 A | 7/2016 |
| JP | 2006-525374 A | 11/2006 |
| JP | 4855550 B2 | 1/2012 |
| JP | 2012-20992 A | 2/2012 |
| JP | 2014-210765 A | 11/2014 |
| JP | 2016-204291 A | 12/2016 |

OTHER PUBLICATIONS

CN105753637 (A), English translation, Jul. 13, 2016, pp. 1-12 (Year: 2016).*
International Search Report (PCT/ISA/210 &PCT/ISA/220) issued in PCT Application No. PCT/JP2017/014648 dated Jul. 4, 2017 with English translation (six pages).
Japanese-language Written Opinion (PCT/ISA/237) issued in PCT Application No. PCT/JP2017/014648 dated Jul. 4, 2017 (four pages).
Henne et al., "A New Method of Synthesizing Organic 1,1,1-Trifluorides", J. Am. Chem. Soc., Dec. 1941, pp. 3478-3479, vol. 63 (two pages).
Whaley et al., "Isomerization During Allylic Fluorination", J. Am. Chem. Soc., Mar. 1948, pp. 1026-1027, vol. 70 (two pages).
Haszeldine "Reactions of Fluorocarbon Radicals, Part V.* Alternative Syntheses for Trifluoromethylacetylene (3:3:3-Trifluoropropyne), and the Influence of Polyfluoro-groups on Adjacent Hydrogen and Halogen Atoms.", J. Chem. Soc., 1951, pp. 2495-2504 (10 pages).

* cited by examiner

*Primary Examiner* — Medhanit W Bahta
(74) *Attorney, Agent, or Firm* — Crowell & Moring LLP

(57) ABSTRACT

A method for producing 1,2-dichloro-3,3,3-trifluoropropene according to the present invention includes the step of reacting 1,1,2,3,3-pentachloropropene with a fluorinating agent where hydrogen fluoride is used as the fluorinating agent.

26 Claims, No Drawings

METHOD FOR PRODUCING
1,2-DICHLORO-3,3,3-TRIFLUOROPROPENE

TECHNICAL FIELD

The present invention relates to a method for producing 1,2-dichloro-3,3,3-trifluoropropene. Furthermore, the present invention relates to a method for producing both 1,2-dichloro-3,3,3-trifluoropropene and 1,2,3-trichloro-3,3-difluoropropene. Furthermore, the present invention relates to a method for producing 1,2,3-trichloro-3,3-difluoropropene.

BACKGROUND TECHNOLOGY 1,2-dichloro-3,3,3-trifluoropropene (hereinafter, may be referred to as 1223xd) is smaller in global warming potential (GWP) than 3,3-dichloro-1,1,1,2,2-pentafluoropropane (225ca) and 1,3-dichloro-1,1,2,2,3-pentafluoropropane (225cb). Therefore, it is expected to be used in various uses, such as cleaning agent, as a compound alternative to these.

There are known various methods as the 1223xd production method.

For example, Patent Publication 1 discloses a method for producing a fluorine-containing propene represented by the general formula of $CF_3CH=CHZ$ (Z is Cl or F.) by using a chlorine-containing compound as the raw material and through a gas-phase fluorination reaction and a dehalogenation reaction. In particular, in Example 4, it is described that 1,2-dichloro-3,3,3-trifluoropropene is formed as a by-product of a gas-phase fluorination reaction and a dehalogenation reaction of 1,1,1,3,3-pentachloropropane (HFC-240fa). Furthermore, Patent Publication 2 discloses a method for producing 1,2-dichloro-3,3,3-trifluoropropene by reacting 1-halogeno-3,3,3-trifluoropropene represented by the general formula of $CF_3CH=CHX$ (X is F, Cl or Br) with chlorine in the presence of a catalyst in a gas phase.

As a reaction under a liquid phase, Non-patent Publication 1 discloses a method of reacting 1,2,3,3,3-pentachloropropene (1220xd) with antimony trifluoride. Furthermore, Non-patent Publication 2 discloses a method of reacting 1,1,2,3,3-pentachloropropene (hereinafter, may be referred to as 1220xa) with antimony trifluoride by using antimony pentachloride as a catalyst. Non-patent Publication 3 discloses a production method by adding potassium hydroxide under solid condition to 1,2,2-trichloro-3,3,3-trifluoropropane as a liquid and then conducting a reflux operation with heating.

PRIOR ART PUBLICATIONS

Patent Publications

Patent Publication 1: JP Patent Application Publication 2012-20992.
Patent Publication 2: JP Patent Application Publication 2014-210765.

Non-Patent Publications

Non-patent Publication 1: A. L. Henne et al., J. Am. Chem. Soc., 1941, p. 3478-3479.
Non-patent Publication 2: A. M. Whaley et al., J. Am. Chem. Soc., 1948, p. 1026-1027.
Non-patent Publication 3: R. N. Haszeldine et al., J. Chem. Soc., 1951, p. 2495-2504.

DISCLOSURE OF THE INVENTION

Task to be Solved by the Invention

It is a task of the present invention to provide a method for efficiently producing 1,2-dichloro-3,3,3-trifluoropropene (1223xd). Furthermore, it is a task of the present invention to provide a method for efficiently producing both 1,2-dichloro-3,3,3-trifluoropropene (1223xd) and 1,2,3-trichloro-3,3-difluoropropene (1222xd). Furthermore, it is a task of the present invention to provide a method for efficiently producing 1,2,3-trichloro-3,3-difluoropropene (1222xd).

Means for Solving the Task

In the production methods described in Non-patent Publications 1 and 2, antimony trifluoride is used as a fluorination agent. In this method, a large amount of waste water, etc. containing organic matter and/or metal is generated and discharged by a post-treatment. Therefore, it becomes necessary to conduct a treatment of the organic metal-containing waste water, etc. Furthermore, in a method of conducting a reaction by dispersing a powdery potassium hydroxide into 1,2,2-trichloro-3,3,3-trifluoropropane in a liquid condition, the reaction system turns into a heterogeneous reaction, and yield is at a medium level (48%). Therefore, from the viewpoint of the industrial production method, it is preferable to be a more efficient production method.

Thus, the present inventors have eagerly conducted a study to solve the above-mentioned task. As a result, we found that 1,2-dichloro-3,3,3-trifluoropropene (1223xd) can be efficiently produced by fluorinating 1,1,2,3,3-pentachloropropene (1220xa) by using hydrogen fluoride as a fluorinating agent, thereby completing the present invention. This fluorination is conducted preferably in a liquid phase or in a gas phase.

Furthermore, the present inventors have found that both 1,2-dichloro-3,3,3-trifluoropropene (1223xd) and 1,2,3-trichloro-3,3-difluoropropene (1222xd) can be efficiently produced by fluorinating 1,1,2,3,3-pentachloropropene (1220xa) by using hydrogen fluoride as a fluorinating agent, thereby completing the present invention. This fluorinating is conducted preferably in a liquid phase or in a gas phase.

Furthermore, the present inventors have found that 1,2,3-trichloro-3,3-difluoropropene (1222xd) can be efficiently produced by fluorinating 1,1,2,3,3-pentachloropropene (1220xa) by using hydrogen fluoride as a fluorinating agent, thereby completing the present invention. This fluorination is conducted preferably in a liquid phase or in a gas phase.

That is, the present invention contains each of the following inventions.

[Invention 1]

A method for producing 1,2-dichloro-3,3,3-trifluoropropene (1223xd) by fluorinating 1,1,2,3,3-pentachloropropene (1220xa) by a reaction with a fluorinating agent, the method being characterized in that hydrogen fluoride is used as the fluorinating agent.

[Invention 2]

The method according to Invention 1, which is characterized in that the reaction is conducted in a liquid phase.

[Invention 3]

The method according to Invention 1, which is characterized in that the reaction is conducted in a gas phase.

[Invention 4]
The method according to any of Inventions 1 to 3, which is characterized in that usage of the hydrogen fluoride is 3 to 40 mol relative to 1 mol of 1,1,2,3,3-pentachloropropene (1220xa).

[Invention 5]
The method according to any of Invention 1, 2 or 4, which is characterized in that the reaction is conducted at 100 to 200° C.

[Invention 6]
The method according to any of Invention 1, 2, 4 or 5, which is characterized in that the reaction is conducted at 140 to 180° C.

[Invention 7]
The method according to any of Invention 1, 3 or 4, which is characterized in that the reaction is conducted at 160 to 600° C.

[Invention 8]
The method according to any of Inventions 1 to 7, which is characterized in that the reaction is conducted in the absence of catalyst.

[Invention 9]
The method according to any of Inventions 1 to 7, which is characterized in that the reaction is conducted in the presence of a catalyst.

[Invention 10]
The method according to any of Invention 1, 3, 4, 7 or 9, which is characterized in that the reaction is conducted by using a catalyst that is a metal oxide, a metal fluoride or a metal compound-supported catalyst.

[Invention 11]
The method according to Invention 10, which is characterized in that the catalyst is subjected to a fluorination treatment to be used in the reaction.

[Invention 12]
The method according to any of Inventions 1 to 11, which is characterized in that the reaction is conducted in the presence of at least one selected from the group consisting of chlorine, oxygen and air.

[Invention 13]
The method according to any of Inventions 1 to 12, which is characterized in that the reaction is conducted in the absence of solvent.

[Invention 14]
The method according to any of Inventions 1 to 13, which is characterized in that 1,2,3-trichloro-3,3-difluoropropene (1222xd), together with 1,2-dichloro-3,3,3-trifluoropropene (1223xd), is formed by the reaction.

[Invention 15]
The method according to any of Inventions 1 to 14, which is characterized by comprising the step of purifying 1,2-dichloro-3,3,3-trifluoropropene (1223xd).

[Invention 16]
The method according to any of Inventions 1 to 15, which is characterized in that 1,2,3-trichloro-3,3-difluoropropene (1222xd) is separated and then is used in the reaction as a raw material for producing 1,2-dichloro-3,3,3-trifluoropropene (1223xd).

[Invention 17]
The method according to any of Inventions 1 to 16, which is characterized by further comprising the step of dehydrochlorinating 1,1,1,2,3,3-hexachloropropane (230da) in a liquid phase in the presence of a Lewis acid catalyst to obtain the 1,1,2,3,3-pentachloropropene (1220xa).

[Invention 18]
The method according to Invention 17, which is characterized in that the Lewis acid catalyst to be used in the dehydrochlorination of 1,1,1,2,3,3-hexachloropropane (230da) comprises a halide of a metal that is at least one selected from the group consisting of aluminum, vanadium, chromium, manganese, iron, cobalt, nickel, copper, zirconium, niobium, molybdenum, ruthenium, rhodium, palladium, silver, tin, antimony, tantalum, and tungsten.

[Invention 19]
The method according to Invention 16 or Invention 17, which is characterized in that the dehydrochlorination is conducted at 50 to 200° C.

[Invention 20]
The method according to any of Inventions 17 to 19, which is characterized by further comprising the step of chlorinating 1,1,3,3-tetrachloropropene (1230za) in a liquid phase in the presence of a Lewis acid catalyst to obtain the 1,1,1,2,3,3-hexachloropropane (230da).

[Invention 21]
The method according to Invention 20, which is characterized in that the Lewis acid catalyst to be used in the chlorination of 1,1,3,3-tetrachloropropene (1230za) comprises a halide of a metal that is at least one selected from the group consisting of aluminum, vanadium, chromium, manganese, iron, cobalt, nickel, copper, zirconium, niobium, molybdenum, ruthenium, rhodium, palladium, silver, tin, antimony, tantalum, and tungsten.

[Invention 22]
The method according to Invention 20 or 21, which is characterized by further comprising the step of dehydrochlorinating 1,1,1,3,3-pentachloropropane (240fa) in a liquid phase in the presence of a Lewis acid catalyst to obtain the 1,1,3,3-tetrachloropropene (1230za).

[Invention 23]
The method according to Invention 22, which is characterized in that the Lewis acid catalyst to be used in the dehydrochlorination of 1,1,1,3,3-pentachloropropane (240fa) comprises a halide of a metal that is at least one selected from the group consisting of aluminum, vanadium, chromium, manganese, iron, cobalt, nickel, copper, zirconium, niobium, molybdenum, ruthenium, rhodium, palladium, silver, tin, antimony, tantalum, and tungsten.

[Invention 24]
The method according to Invention 22 or 23, which is characterized in that, when conducting the dehydrochlorination of 1,1,1,3,3-pentachloropropane (240fa) as a first step, the chlorination of 1,1,3,3-tetrachloropropene (1230za) as a second step and the dehydrochlorination of 1,1,1,2,3,3-hexachloropropane (230da) as a third step in this order, the Lewis acid catalyst used in the first step is reused in the second and third steps as the Lewis acids of the second and third steps.

[Invention 25]
The method according to Invention 24, which is characterized in that the Lewis acid catalyst of the first step comprises aluminum chloride or ferric chloride.

[Invention 26]
The method according to Invention 24 or 25, which is characterized in that the reaction of the first step is conducted at 40 to 200° C., the reaction of the second step is conducted at −20 to +110° C., and the reaction of the third step is conducted at 50 to 200° C.

[Invention 27]
The method according to Invention 26, which is characterized in that the reaction temperature of the third step is higher than at least the reaction temperature of the second step.

[Invention 28]

A method for producing both 1,2-dichloro-3,3,3-trifluoropropene (1223xd) and 1,2,3-trichloro-3,3-difluoropropene (1222xd) by reacting 1,1,2,3,3-pentachloropropene (1220xa) with hydrogen fluoride.

[Invention 29]

The method according to Invention 28, which is characterized in that the reaction is conducted in a liquid phase.

[Invention 30]

The method according to Invention 28, which is characterized in that the reaction is conducted in a gas phase.

[Invention 31]

The method according to any of Inventions 28 to 30, which is characterized in that the reaction is conducted in the presence of a catalyst.

[Invention 32]

The method according to any of Inventions 28 to 30, which is characterized in that the reaction is conducted in the absence of catalyst.

[Invention 33]

The method according to any of Inventions 28 to 32, which is characterized by comprising the step of separating 1,2-dichloro-3,3,3-trifluoropropene (1223xd) and 1,2,3-trichloro-3,3-difluoropropene (1222xd).

[Invention 34]

The method according to any of Inventions 28 to 33, which is characterized in that the reaction is conducted in the presence of at least one selected from the group consisting of chlorine, oxygen and air.

[Invention 35]

A method for producing 1,2,3-trichloro-3,3-difluoropropene (1222xd) by reacting 1,1,2,3,3-pentachloropropene (1220xa) with hydrogen fluoride.

[Invention 36]

The method according to Invention 35, which is characterized in that the reaction is conducted in a liquid phase.

[Invention 37]

The method according to Invention 35, which is characterized in that the reaction is conducted in a gas phase.

[Invention 38]

The method according to Invention 36, which is characterized in that the reaction is conducted at 100 to 140° C.

[Invention 39]

The method according to any of Inventions 35 to 38, which is characterized in that the reaction is conducted in the presence of a catalyst.

[Invention 40]

The method according to any of Inventions 35 to 38, which is characterized in that the reaction is conducted in the absence of catalyst.

[Invention 41]

The method according to any of Inventions 35 to 40, which is characterized in that the reaction is conducted in the presence of at least one selected from the group consisting of chlorine, oxygen and air.

In a preferable mode of the present invention, the fluorination reaction of 1,1,2,3,3-pentachloropropene (1220xa) is conducted in a liquid phase in the absence of catalyst by using hydrogen fluoride as the fluorinating agent. In the reaction, it is preferable that usage of hydrogen fluoride is 3 to 40 mol relative to 1 mol of 1220xa. The reaction is conducted preferably at 100 to 200° C., particularly preferably at 140 to 180° C. Furthermore, the reaction is conducted preferably in the absence of solvent. By the reaction, 1,2-dichloro-3,3,3-trifluoropropene (1223xd) is produced. This 1223xd is produced in Z form (1223zd(Z)), E form (1223zd(E)), or both. It is produced preferably in Z form.

Furthermore, in another preferable mode of the present invention, the fluorination reaction of 1220xa is conducted in a gas phase in the presence of a catalyst by using hydrogen fluoride as the fluorinating agent. In the reaction, it is preferable that usage of hydrogen fluoride is 3 to 40 mol relative to 1 mol of 1220xa. The reaction is conducted preferably at 160 to 600° C., more preferably 180 to 500° C., particularly preferably 200 to 400° C., still more preferably 210 to 350° C. It is preferable to use a metal-containing catalyst as the catalyst. It is more preferable to use a metal oxide, a metal fluoride, or a metal compound-supported catalyst. It is more preferable to use a catalyst containing at least one metal selected from the group consisting of aluminum, chromium, titanium, manganese, iron, nickel, cobalt, copper, magnesium, zirconium, molybdenum, zinc, tin, lanthanum, niobium, tantalum, and antimony. Catalysts containing these metals that have been partially or totally fluorinated are more preferable. Furthermore, the reaction is conducted in the presence or absence of at least one selected from the group consisting of chlorine, oxygen and air. It is conducted preferably in the presence of at least one selected from the group consisting of chlorine, oxygen and air. Furthermore, 1223xd is produced by the reaction. This 1223xd is produced in Z form, E form or both. It is produced preferably in Z form.

Furthermore, in another preferable mode of the present invention, the fluorination reaction of 1220xa is conducted in a gas phase in the absence of catalyst by using hydrogen fluoride as the fluorinating agent. In the reaction, it is preferable that usage of hydrogen fluoride is 3 to 40 mol relative to 1 mol of 1220xa. The reaction is conducted preferably at 160 to 600° C., more preferably 180 to 500° C., particularly preferably 200 to 400° C., still more preferably 210 to 350° C. Furthermore, the reaction is conducted in the presence or absence of at least one selected from the group consisting of chlorine, oxygen and air. It is conducted preferably in the presence of at least one selected from the group consisting of chlorine, oxygen and air. Furthermore, 1223xd is produced by the reaction. This 1223xd is produced in Z form, E form or both. It is produced preferably in Z form.

Furthermore, in another preferable mode of the present invention, the fluorination reaction of 1220xa is conducted in a liquid phase in the absence of catalyst by using hydrogen fluoride as the fluorinating agent. In the reaction, it is preferable that usage of hydrogen fluoride is 3 to 40 mol relative to 1 mol of 1220xa. The reaction is conducted preferably at 100 to 200° C. Furthermore, the reaction is conducted preferably in the absence of solvent. By the reaction, both 1223xd and 1,2,3-trichloro-3,3-difluoropropene (1222xd) are produced. When both are produced, this 1222xd is produced in Z form (1222xd(Z)), E form (1222xd(E)) or both. When both are produced, 1223xd is produced preferably in Z form.

Furthermore, in another preferable mode of the present invention, the fluorination reaction of 1220xa is conducted in a gas phase in the presence of a catalyst by using hydrogen fluoride as the fluorinating agent. In the reaction, it is preferable that usage of hydrogen fluoride is 3 to 40 mol relative to 1 mol of 1220xa. The reaction is conducted preferably at 160 to 300° C., more preferably 180 to 280° C., particularly preferably 180 to 270° C., still more preferably 180 to 260° C. It is preferable to use a metal-containing catalyst as the catalyst. It is more preferable to use a metal oxide, a metal fluoride, or a metal compound-supported catalyst. It is more preferable to use a catalyst containing at least one metal selected from the group consisting of aluminum, chromium, titanium, manganese, iron, nickel, cobalt, copper, magnesium, zirconium, molybdenum, zinc, tin, lanthanum, niobium, tantalum, and antimony. Catalysts containing these metals that have been partially or totally fluorinated are more preferable. Furthermore, the reaction is conducted in the presence or absence of at least one selected from the group consisting of chlorine, oxygen and air. It is conducted preferably in the presence of at least one selected from the group consisting of chlorine, oxygen and air. By the reaction, both 1223xd and 1,2,3-trichloro-3,3-difluoropropene (1222xd) are produced. When both are produced, this 1223xd is produced in Z form, E form or both, and this 1222xd is produced in Z form (1222xd(Z)), E form (1222xd (E)) or both. When both are produced, 1223xd is produced preferably in Z form.

Furthermore, in another preferable mode of the present invention, the fluorination reaction of 1220xa is conducted in a gas phase in the absence of catalyst by using hydrogen fluoride as the fluorinating agent. In the reaction, it is preferable that usage of hydrogen fluoride is 3 to 40 mol relative to 1 mol of 1220xa. The reaction is conducted preferably at 160 to 300° C., more preferably 180 to 280° C., particularly preferably 180 to 270° C., still more preferably 180 to 260° C. Furthermore, the reaction is conducted in the presence or absence of at least one selected from the group consisting of chlorine, oxygen and air. It is conducted preferably in the presence of at least one selected from the group consisting of chlorine, oxygen and air. By the reaction, both 1223xd and 1,2,3-trichloro-3,3-difluoropropene (1222xd) are produced. When both are produced, this 1223xd is produced in Z form, E form or both, and this 1222xd is produced in Z form (1222xd(Z)), E form (1222xd (E)) or both. When both are produced, 1223xd is produced preferably in Z form.

Furthermore, in another preferable mode of the present invention, the fluorination reaction of 1220xa is conducted in a liquid phase in the absence of catalyst by using hydrogen fluoride as the fluorinating agent. In the reaction, it is preferable that usage of hydrogen fluoride is 3 to 40 mol relative to 1 mol of 1220xa. The reaction is conducted preferably at 100 to 200° C., particularly preferably at 100 to 140° C. Furthermore, the reaction is conducted preferably in the absence of solvent. By the reaction, 1222xd is produced, and this 1222xd is in Z form (1222xd(Z)), E form (1222xd(E)) or both. It is produced preferably in Z form.

Furthermore, in another preferable mode of the present invention, the fluorination reaction of 1220xa is conducted in a gas phase in the presence of a catalyst by using hydrogen fluoride as the fluorinating agent. In the reaction, it is preferable that usage of hydrogen fluoride is 3 to 40 mol relative to 1 mol of 1220xa. The reaction is conducted preferably at 160 to 280° C., particularly preferably 180 to 270° C., still more preferably 180 to 260° C. It is preferable to use a metal-containing catalyst as the catalyst. It is more preferable to use a metal oxide, a metal fluoride, or a metal compound-supported catalyst. It is more preferable to use a catalyst containing at least one metal selected from the group consisting of aluminum, chromium, titanium, manganese, iron, nickel, cobalt, copper, magnesium, zirconium, molybdenum, zinc, tin, lanthanum, niobium, tantalum, and antimony. Catalysts containing these metals that have been partially or totally fluorinated are more preferable. Furthermore, the reaction is conducted in the presence or absence of at least one selected from the group consisting of chlorine, oxygen and air. It is conducted preferably in the presence of at least one selected from the group consisting of chlorine, oxygen and air. By the reaction, 1222xd is produced, and this 1222xd is produced in Z form (1222xd(Z)), E form (1222xd(E)) or both. It is produced preferably in Z form.

Furthermore, in another preferable mode of the present invention, the fluorination reaction of 1220xa is conducted in a gas phase in the absence of catalyst by using hydrogen fluoride as the fluorinating agent. In the reaction, it is preferable that usage of hydrogen fluoride is 3 to 40 mol relative to 1 mol of 1220xa. The reaction is conducted preferably at 160 to 280° C., particularly preferably 180 to 270° C., still more preferably 180 to 260° C. Furthermore, in the reaction, the contact time is preferably 1 to 100 seconds, particularly preferably 10 to 50 seconds. Furthermore, the reaction is conducted in the presence or absence of at least one selected from the group consisting of chlorine, oxygen and air. It is conducted preferably in the presence of at least one selected from the group consisting of chlorine, oxygen and air. By the reaction, 1222xd is produced, and this 1222xd is produced in Z form (1222xd(Z)), E form (1222xd(E)) or both. It is produced preferably in Z form.

In the present specification, producing both 1223xd and 1222xd means that at least 1223xd and 1222xd are produced by a reaction according to the present invention. 1222xd is produced by preferably at least 0.0001 mol, particularly preferably at least 0.001 mol, per 1 mol of 1223xd.

By the present invention, it is possible to efficiently produce 1,2-dichloro-3,3,3-trifluoropropene (1223xd). That is, according to the present invention, it is possible to easily produce 1,2-dichloro-3,3,3-trifluoropropene (1223xd) with high selectivity by using 1,1,2,3,3-pentachloropropene (1220xa) as the raw material.

Furthermore, it is possible by the present invention to efficiently produce both 1,2-dichloro-3,3,3-trifluoropropene (1223xd) and 1,2,3-trichloro-3,3-difluoropropene (1222xd).

Furthermore, it is possible by the present invention to efficiently produce 1,2,3-trichloro-3,3-difluoropropene (1222xd).

MODE FOR IMPLEMENTING THE INVENTION

In the following, the present invention is explained. The present invention is not limited to the following embodiments. Within the scope of not deviating from the gist of the present invention, those obtained by suitably modifying and/or improving the following embodiments are also treated as being included in the present invention.

The method of the present invention is a method for producing 1,2-dichloro-3,3,3-trifluoropropene (1223xd) by fluorinating 1,1,2,3,3-pentachloropropene (1220xa) by a reaction with a fluorinating agent and is characterized in that the hydrogen fluoride is used as the fluorinating agent. In the method of the present invention, the reaction may be conducted in a liquid phase or may be conducted in a gas phase.

In one mode of the present invention, the method of the present invention is characterized in that 1,1,2,3,3-pentachloropropene (1220xa) as the raw material is reacted with hydrogen fluoride in a liquid phase. Furthermore, in another mode of the present invention, the method of the present invention is characterized in that 1,1,2,3,3-pentachloropropene (1220xa) as the raw material is reacted with hydrogen fluoride in a gas phase.

In the reaction according to the present invention, 1,1,2, 3,3-pentachloropropene (1220xa) used as the raw material is a publicly-known compound and can be produced by various methods. One example of the production method is mentioned hereafter, but this does not prevent other methods from being adopted. It is, however, possible by adopting the after-mentioned production method to advantageously produce 1,1,2,3,3-pentachloropropene (1220xa).

In the case of a liquid-phase reaction of 1,1,2,3,3-pentachloropropene (1220xa) with hydrogen fluoride in one mode of the present invention, usage of hydrogen fluoride is normally 3 to 40 mol, preferably 5 to 30 mol, more preferably 10 to 20 mol, relative to 1 mol of 1,1,2,3,3-pentachloropropene (1220xa) as the raw material.

In the case of a gas-phase reaction of 1,1,2,3,3-pentachloropropene (1220xa) with hydrogen fluoride in another mode of the present invention, usage of hydrogen fluoride is normally 3 to 40 mol, preferably 3 to 30 mol, more preferably 3 to 20 mol, particularly preferably 3 to 10 mol.

This usage of hydrogen fluoride is indicated relative to the supply amount of 1,1,2,3,3-pentachloropropene (1220xa) to be used, in case that the reaction type is a batch type or half-batch type. In the case of a continuous type, it is indicated relative to the steady amount of 1,1,2,3,3-pentachloropropene (1220xa) existing in the reactor. If the amount of hydrogen fluoride is less than 3 mol, it is less than the theoretical amount of hydrogen fluoride necessary to form 1,2-dichloro-3,3,3-trifluoropropene (1223xd). This may lower both selectivity of the reaction and yield of the target. On the other hand, if the amount of hydrogen fluoride exceeds 40 mol, the amount of hydrogen fluoride not involved in the reaction increases. Therefore, it is not economically preferable from the viewpoint of productivity. These matters, however, do not prevent the use of hydrogen fluoride by less than 3 mol or greater than 40 mol relative to 1 mol of 1220xa.

In the reaction according to the present invention, it is preferable from the viewpoint of industrial production to separate the unreacted hydrogen fluoride from the reaction product and then return it to the reaction system. The separation of hydrogen fluoride from the reaction product can be conducted by a publicly-known means. For example, a method of distilling the reaction product, etc. can be cited.

In the reaction according to the present invention, the reaction temperature is not particularly limited, as long as the target is formed.

In one mode of the present invention, temperature of the liquid phase reaction of 1,1,2,3,3-pentachloropropene (1220xa) with hydrogen fluoride is normally 50 to 300° C., preferably 100 to 200° C. In particular, 140 to 180° C. is particularly preferable, since it is possible to more advantageously produce 1,2-dichloro-3,3,3-trifluoropropene (1223xd). Furthermore, in the case that both 1,2-dichloro-3,3,3-trifluoropropene (1223xd) and 1,2,3-trichloro-3,3-difluoropropene (1222xd) are produced, 50 to 300° C. is preferable, and 100 to 200° C. is particularly preferable. Furthermore, in order to more advantageously produce 1,2,3-trichloro-3,3-difluoropropene (1222xd), 100 to 200° C. is preferable, and 100 to 140° C. is particularly preferable.

In one mode of the present invention, temperature of the gas-phase reaction of 1,1,2,3,3-pentachloropropene (1220xa) with hydrogen fluoride is not particularly limited, as long as the reaction can be conducted in a gas phase. It is preferable to conduct that at a temperature at which the reaction raw material turns into a gaseous condition, or higher. In another mode of the present invention, the gas-phase reaction is conducted normally at 160° C. or higher, preferably 180° C. or higher, more preferably 200° C. or higher. Since it is possible to more advantageously produce 1223xd, 210° C. or higher is particularly preferable. The upper limit of the gas-phase reaction temperature is not particularly limited. The gas-phase reaction is conducted normally at 600° C. or lower, preferably 500° C. or lower. Since it is possible to more advantageously suppress coking of the reaction raw material, 400° C. or lower is more preferable, still more preferably 350° C. or lower, particularly preferably 300° C. or lower. In another mode of the present invention, temperature of the gas-phase reaction may be in any temperature range obtained by freely combining the above-mentioned lower limit temperature and the upper limit temperature. In the case of producing both 1,2-dichloro-3,3,3-trifluoropropene (1223xd) and 1,2,3-trichloro-3,3-difluoropropene (1222xd), 160 to 300° C. is preferable, more preferably 180 to 280° C., particularly preferably 180 to 270° C., still more preferably 180 to 260° C. Furthermore, in order to more advantageously produce 1,2,3-trichloro-3,3-difluoropropene (1222xd), 160 to 280° C. is preferable, more preferably 180 to 270° C., particularly preferably 180 to 260° C.

In the reaction according to the present invention, pressure is not limited. It may be conducted under reduced pressure, under ordinary pressure (under atmospheric pressure) or under pressurization.

In one mode of the present invention, the reaction pressure of the liquid-phase reaction is normally 0.1 to 10 MPaG (meaning gauge pressure, hereinafter the same), preferably 1.5 to 6 MPaG, more preferably 2.0 to 4.5 MPaG. If it is lower than 0.1 MPaG, it cannot be increased to a preferable reaction temperature due to reflux of the unreacted hydrogen fluoride. Therefore, it does not become a practical production method. If it exceeds 10 MPaG, the cost of reactor's pressure-proof design increases. Therefore, it is not economically preferable. These matters, however, do not prevent conducting the reaction under a pressure that is lower than 0.1 MPaG or higher than 10 MPaG.

In another mode of the present invention, it is preferable to conduct the gas-phase reaction under reduced pressure or under ordinary pressure. It is particularly preferable to conduct that under a pressure in the vicinity of ordinary pressure. As the pressure control method, it is possible to control the pressure by an arbitrary appropriate means, such as a distillation tower and/or water condenser, which is installed at the reactor's outlet, and a pressure control valve.

In the reaction according to the present invention, it is optional to use or not to use catalyst.

(1) In the liquid-phase reaction, it is preferable to use no catalyst, since the reaction's post-treatment is easy, and it is possible to efficiently produce 1,2-dichloro-3,3,3-trifluoropropene (1223xd). In the case of using catalyst in the liquid-phase reaction, it is possible to use an arbitrary appropriate catalytic amount of a halide of a metal of titanium, tin, iron, antimony, tantalum, niobium, molybdenum, etc. or its mixture.

(2) In the gas-phase reaction too, it is optional to use or not to use catalyst. In the case of using a catalyst in the gas-phase reaction, the catalyst may be an unsupported catalyst or a supported catalyst.

As the unsupported catalyst, a metal compound is preferable, and metal compound, such as metal oxide or metal fluoride, is more preferable. Herein, the metal fluoride refers to one having at least a bond between metal atom and fluorine atom. One that a bond between metal atom and fluorine atom is confirmed, for example, by IR, XRD or XPS can be used as the catalyst in the gas-phase reaction. Furthermore, the type of metal contained in these metal compounds is not particularly limited. It is possible to cite, for example, at least one metal selected from the group consisting of aluminum, chromium, titanium, manganese, iron, nickel, cobalt, copper, magnesium, zirconium, molybdenum, zinc, tin, lanthanum, niobium, tantalum, and antimony. In particular, at least one metal selected from the group consisting of aluminum, chromium, manganese, zirconium, titanium and magnesium is preferable. The metal may be alone or a composite metal made up of at least two metals.

The method for preparing the metal fluoride is not particularly limited. For example, such metal fluoride can be prepared by conducting a fluorination treatment on a metal compound such as metal oxide. The type of this metal oxide is not particularly limited. For example, it is possible to cite an oxide of at least one metal selected from the group consisting of aluminum, chromium, titanium, manganese, iron, nickel, cobalt, copper, magnesium, zirconium, molybdenum, zinc, tin, lanthanum, niobium, tantalum, and antimony. In particular, an oxide of at least one metal selected from the group consisting of aluminum, chromium, manganese, zirconium, titanium and magnesium is preferable. The metal contained in the metal oxide may be alone. Alternatively, it may be used as an oxide of a composite metal made up of at least two metals. Although some metal oxides have different crystal systems, any of them can be used. For example, alumina has γ-alumina and α-alumina. Titania has anatase and rutile crystal forms. Although any crystal form of the metal oxide will do, γ-alumina is preferable in alumina due to its large surface area. Besides the metal oxide, it is possible to prepare a metal fluoride by using one that is capable of turning into a metal fluoride by the fluorination treatment.

The composite metal is preferably one containing as a primary component at least one metal selected from the group consisting of aluminum, chromium, manganese, zirconium, titanium and magnesium, and as a secondary component at least one metal selected from the group consisting of aluminum, chromium, titanium, manganese, iron, nickel, copper, cobalt, magnesium, zirconium, molybdenum, zinc, tin, lanthanum, niobium, tantalum, and antimony.

As preferable oxides of such composite metals, it is possible to cite, for example, a combination of alumina and chromia, a combination of alumina and zirconia, a combination of alumina and titania, and a combination of alumina and magnesia. Of these, one containing 50 atomic % or greater of aluminum is particularly preferable, and one containing 80 atomic % or greater of aluminum is more preferable. If it is 50 atomic % or greater, it is possible to make the reaction progress at a good conversion rate.

The fluorination treatment method on the metal compound is not particularly limited. For example, it may be conducted by making a contact between a fluorinating agent, such as hydrogen fluoride, a fluorinated hydrocarbon or a fluorochlorinated hydrocarbon, and the above-mentioned metal compound (for example, a metal oxide or a composite metal oxide). Normally, it is preferable to gradually conduct this fluorination treatment. In the case of conducting the fluorination treatment by using hydrogen fluoride, it is accompanied by a large heat generation. Therefore, it is preferable to fluorinate a metal compound by a diluted hydrogen fluoride at a relatively low temperature at first and then conduct that as gradually increasing concentration and/or temperature. At the final stage, it is preferable to conduct that at a temperature that is the reaction temperature or higher of the reaction according to the present invention. Besides this condition, in order to make the reaction progress stably, it is preferable to conduct the fluorination treatment by hydrogen fluoride at 200° C. or higher, 400° C. or higher, more preferably 500° C. or higher. There is no particular upper limit of temperature. If it exceeds 900° C., it is difficult in terms of heat resistance of the fluorination treatment apparatus. Practically, it is preferable to conduct that at 600° C. or lower. In this manner, in order to make the reaction progress stably, it is preferable to previously prepare a metal fluoride by conducting a fluorination treatment on a metal compound (for example, a metal oxide or a composite metal oxide) by a fluorinating agent, such as hydrogen fluoride, a fluorinated hydrocarbon or a fluorochlorinated hydrocarbon, at a temperature that is a predetermined reaction temperature or higher, and then use it as a catalyst of the gas-phase reaction of the present invention.

To be used in the reaction, it is preferable to conduct a fluorination treatment on the catalyst to be used in the gas-phase reaction. This fluorination treatment can be conducted on the catalyst (preferably a metal compound) in accordance with the above-mentioned metal fluoride preparation method's example.

In the gas-phase reaction, it is optional to use a metal compound-supported catalyst as the catalyst. As a support of this supported catalyst, it is optional to use carbon or the above-mentioned metal (containing the composite metal) as the unsupported catalyst. The metal used as the support may be the above-mentioned metal oxide or metal fluoride as the unsupported catalyst. Specifically, as the support, it is optional to singly use an oxide of at least one metal selected from the group consisting of aluminum, chromium, titanium, manganese, iron, nickel, cobalt, copper, magnesium, zirconium, molybdenum, zinc, tin, lanthanum, niobium, tantalum and antimony, preferably an oxide of at least one metal selected from the group consisting of aluminum, chromium, manganese, zirconium, titanium and magnesium. Alternatively, it is optional to use a composite metal oxide as the support. These may be partially or totally fluorinated into fluorinated compounds to be used as the supports. The composite metal oxide is preferably an oxide containing as a primary component at least one metal selected from the group consisting of aluminum, chromium, manganese, zirconium, titanium and magnesium, and as a secondary component at least one metal selected from the group consisting of aluminum, chromium, titanium, manganese, iron, nickel, copper, cobalt, magnesium, zirconium, molybdenum, zinc, tin, lanthanum, niobium, tantalum, and antimony.

As the metal contained in the metal compound to be supported, it is possible to cite aluminum, chromium, titanium, manganese, iron, nickel, cobalt, copper, magnesium, zirconium, molybdenum, zinc, tin, lanthanum, niobium, tantalum, antimony, etc. Of these, aluminum, chromium, titanium, iron, nickel, cobalt, copper, zirconium, zinc, tin, lanthanum, niobium, tantalum, and antimony are preferable. These metals are supported in the form of fluorides, chlorides, fluorochlorides, oxyfluorides, oxychlorides, oxyfluorochlorides, etc. on the support. Such metal compounds may be singly supported, or at least two of them may be supported together.

As the metal compound to be supported, specifically, it is possible to use chromium nitrate, chromium trichloride, potassium dichromate, titanium trichloride, manganese nitrate, manganese chloride, ferric chloride, nickel nitrate, nickel chloride, cobalt nitrate, cobalt chloride, antimony pentachloride, magnesium chloride, magnesium nitrate, zirconium chloride, zirconium oxychloride, zirconium nitrate, copper(II) chloride, zinc(II) chloride, lanthanum nitrate, tin tetrachloride, etc. It is, however, not limited to these.

It is optional to conduct a fluorination treatment on a catalyst prepared by supporting the above-mentioned metal compound on the support prior to its use, in order to make the reaction progress stably, and it is preferable to do that. That is, in a gas-phase reaction according to the present invention, the catalyst may be a catalyst prepared by conducting a fluorination treatment on the metal compound-supported catalyst. In this case, it is preferable to conduct a fluorination process in advance with a fluorinating agent, such as hydrogen fluoride, a fluorinated hydrocarbon, or a fluorochlorinated hydrocarbon, by a method similar to the above-mentioned metal compound (e.g., a metal oxide or a complex metal oxide) fluorination treatment to be used as a catalyst of the gas-phase reaction of the present invention.

Herein, in case that the support is a metal oxide and that the support is totally covered with a metal compound layer as the supported substance, the supported substance rather than the support is mainly subjected to the fluorination treatment in the fluorination treatment step. Therefore, the supported substance acts mainly as a catalyst of the reaction according to the present invention. In case that the support is a metal oxide and that the support is not totally covered with a layer of a metal compound as the supported substance, the support together with the supported substance is also subjected to the fluorination treatment in the fluorination treatment step. Therefore, the support together with the supported substance may act as a catalyst in the reaction according to the present invention. In this way, in case that the support together with the supported substance acts as a catalyst, it may act as a complex metal fluoride similar to the unsupported catalyst, not as the supported catalyst.

In the gas-phase reaction, as preferable specific examples of the catalyst, it is possible to cite fluorinated alumina, fluorinated zirconia, fluorinated chromia, and chromium-supported activated carbon. Fluorinated alumina, fluorinated zirconia and fluorinated chromia are particularly preferable. It is preferable to previously conduct a fluorination treatment on these catalysts prior to the reaction.

The percentage of mass of the metal relative to the total mass of the catalyst including the support and the supported substance is 0.1 to 80 mass %, preferably 1 to 50 mass %. If it is 0.1 mass % or greater, it is possible to obtain a good catalytic effect. If it is 80 mass % or less, it is possible to achieve a stable supporting. In case that the supported substance is a solid metal salt, the percentage of mass of the metal relative to the total mass of the catalyst is 0.1 to 40 mass %, preferably 1 to 30 mass %.

In the liquid-phase reaction according to the present invention, it is also possible to use solvent in view of the reaction homogeneity and operability after the reaction. The solvent type to be used is not particularly limited, as long as it can dissolve 1,1,2,3,3-pentachloropropene (1220xa) as the raw material. In particular, it is preferably an organic compound that has a boiling point higher than that of 1,2-dichloro-3,3,3-trifluoropropene (1223xd) as the product and that is not fluorinated by hydrogen fluoride during the reaction. As examples of such solvent, it is possible to cite tetramethylene sulfone (sulfolane), perfluoroalkanes, perfluoroalkenes, hydrofluorocarbons, etc., but it is not limited to these. The amount of the solvent to be used is not particularly limited, as long as it can dissolve 1,1,2,3,3-pentachloropropene (1220xa) as the raw material. It is preferably 80 mass % or less, more preferably 40 mass % or less, relative to 1,1,2,3,3-pentachloropropene (1220xa) as the raw material. Normally, it is preferable to not use solvent from the viewpoint of productivity and economy.

In the reaction according to the present invention, the reaction time is not particularly limited. It is preferable to judge the time when generation of hydrogen chloride produced as a by-product by the reaction between 1,1,2,3,3-pentachloropropene (1220xa) as the raw material and hydrogen fluoride has stopped, as the end point of the reaction.

Normally, the time when increase of the reaction pressure has stopped is judged as the end point of the reaction. It is preferable that the reaction time in the gas-phase reaction has the same meaning as that the after-mentioned contact time.

Normally, in the gas-phase flow manner reaction, the value (second(s)) obtained by dividing the volume A (mL) of the reaction zone by the raw material supply rate B (mL/second(s)) is used many times when productivity is discussed and is referred to as contact time. In case that the reaction zone is equipped with catalyst, the volume (mL) of the catalyst is regarded as the above-mentioned A. The value of B indicates the volume of the raw material gas to be introduced into the reactor per second. In this case, the raw material gas is regarded as ideal gas, and the value of B is calculated from the raw material gas mol number, pressure and temperature. In the reactor, it is possible that by-production of other compounds other than the raw material and the target and/or the change of mol number occur, but it is not considered when calculating the contact time.

The contact time is decided depending on the reaction raw material, the reaction temperature, the reactor shape, the catalyst type, etc., used in the method of the present invention. Therefore, it is desirable to suitably adjust the reaction raw material supply rate to optimize the contact time, for each of the reaction raw material, the reaction apparatus set temperature, the reactor's shape, and the catalyst type.

The optimum contact time in the present invention is 0.01 to 500 seconds, preferably 0.1 to 250 seconds, more preferably 1 to 150 seconds. This contact time may be suitably changed in accordance with the reaction pressure.

In the gas-phase reaction, from the viewpoint of the reaction efficiency, it is preferable to conduct an operation to achieve a trade-off relationship between the reaction temperature and the contact time to make a contact of the reaction raw material, such as 1223xd and/or hydrogen fluoride, with the catalyst. That is, it is preferable to conduct an operation such that the contact time is shortened if the reaction temperature is increased and that the contact time is prolonged if the reaction temperature is lowered.

In the reaction according to the present invention, the reactor is not particularly limited, but it is preferable to use a reactor suitable for the liquid-phase reaction or the gas-phase reaction. Such liquid-phase reactor or gas-phase reactor is publicly known in the present technology. The reactor is preferably made of a material such as stainless steel, Hastelloy (trade mark), Monel (trade mark), platinum, carbon, fluororesin or one lined with one of these, but it is not limited to these. Furthermore, the reactor may be filled with a filler such as Raschig ring or Paul ring. These materials are preferably made of a material such as stainless steel, Hastelloy (trade mark) or Monel (trade mark).

In the reaction according to the present invention, it is optional to introduce an additive, such as chlorine, oxygen or air, to the reaction system. The introduction of such additive into the reaction system is expected to bring the effect of preventing coking of the reaction material and/or prolonging the catalyst lifetime. The amount of such additive to be introduced into the reaction system is not particularly limited. In general, it is 0.01 to 10 mol %, more preferably 0.1 to 5 mol %, relative to 1,2-dichloro-3,3,3-trifluoropropene (1223xd). Furthermore, such additive may be introduced singly or in combination. Furthermore, it can also be introduced by mixture with an inert gas (for example, noble gas such as nitrogen, helium or argon, and a chlorofluorocarbon gas inert to the reaction).

In the reaction according to the present invention, it is possible to adopt either reaction mode of gas-phase reaction or liquid-phase reaction. Furthermore, the reaction according to the present invention can be conducted by any manner of batch type, half-batch type, and continuous type, and a suitable combination of these reaction modes and manners can be adopted. In the case of using catalyst in a continuous-type gas-phase reaction, the method of holding catalyst may be any of fixed bed, fluidized bed, movable bed, etc. It is easy and preferable to conduct that by a fixed bed.

The procedure of the reaction according to the present invention is not particularly limited, as long as it does not impair the effect of the present invention. In the following, its one example is shown.

In the batch type operation or half-batch type operation, for example, there is exemplified a procedure, etc. to introduce a predetermined amount of a predetermined raw material into the reactor, introduce a predetermined amount of solvent if it is desired, and conduct the reaction under a predetermined condition. In the case of using catalyst, it is preferable to previously put the catalyst into the reactor. The procedure to introduce the raw material into the reactor is not particularly limited. It is optional to introduce 1,1,2,3,3-pentachloropropene (1220xa) into the reactor and then introduce hydrogen fluoride into the reactor. At this time, in the case of introducing a predetermined amount of a predetermined solvent if it is desired, it is optional to introduce a part or the total of the solvent into the reactor prior to introducing hydrogen fluoride into the reactor. It is optional to introduce the solvent by a separate flow or in mixture into the reactor at the same time when hydrogen fluoride is introduced.

In the continuous-type operation, for example, there is exemplified a procedure, etc. to introduce predetermined amounts of 1,1,2,3,3-pentachloropropene (1220xa) and hydrogen fluoride into the reactor by separate flows and conduct the liquid-phase reaction under a predetermined condition. If its use is desired, it is optional to introduce solvent into the reactor to be separate from 1,1,2,3,3-pentachloropropene (1220xa) and hydrogen fluoride. Alternatively, it may be introduced into the reactor in the form of 1,1,2,3,3-pentachloropropene (1220xa) solution and hydrogen fluoride solution.

In the continuous-type operation, for example, there is exemplified a procedure, etc. to introduce predetermined amounts of 1,1,2,3,3-pentachloropropene (1220xa) and hydrogen fluoride and conduct the gas-phase reaction under a predetermined condition. These reaction raw materials are introduced into the reaction system (reactor) by separate flows or the same flow, optionally together with an inert gas (for example, noble gas such as nitrogen, helium or argon, and a chlorofluorocarbon gas inert to the reaction). In the case of using catalyst, it is preferable to previously put the catalyst into the reaction system. Furthermore, if it is desired, an additive, such as chlorine, oxygen or air, is introduced into the reaction system by a flow separate from the reaction raw materials or by the same flow. This additive may be introduced together with the inert gas. These reaction raw materials and the additive are preferably in the gas form when introduced into the reaction system. According to need, these reaction raw materials and the additive are turned into the gas form by a vaporizer and then introduced into the reaction system. In the reaction system, the reaction is conducted under a predetermined condition to obtain a reaction product containing 1223xd.

In the reaction according to the present invention, the method of purifying 1,2-dichloro-3,3,3-trifluoropropene (1223xd) from the obtained reaction product is not particularly limited. It is possible to adopt a publicly known purification method. According to need, it is optional to conduct a treatment to remove a chlorine component and/or acid component, which may be contained in the reaction product. Furthermore, it is optional to conduct a dehydration treatment or the like to remove water, optionally in combination with the chlorine component and/or acid component removal treatment. For example, the reaction product is allowed to flow through a cooled condenser for condensation, then washed with water and/or an alkali solution to remove the chlorine component, the acid component, etc., and then dried with a desiccant such as zeolite or activated carbon, followed by a normal distillation operation. With this, it is possible to obtain 1,2-dichloro-3,3,3-trifluoropropene (1223xd) of high purity.

In case that 1,1,2,3,3-pentachloropropene (1220xa) as the unreacted raw material exists in the reaction product and/or that 1,2,3-trichloro-3,3-difluoropropene (1222xd) exists as a by-product therein, it is possible to singly separate and recover these compounds from the reaction product by a normal distillation operation. The separated 1,1,2,3,3-pentachloropropene (1220xa) can be reused as the raw material of the reaction according to the present invention. Furthermore, 1,2,3-trichloro-3,3-difluoropropene (1222xd) itself may be used for various uses. In some cases, it may be obtained as a mixture of stereoisomers of cis form (1222xd(Z)) and trans form (1222xd(E)). Therefore, these stereoisomers may be separated from each other by a purification operation such as distillation and then may be used for their respective various uses. In one mode of the present invention, 1222xd is obtained as cis form (1222xd(Z)). In another mode, it is obtained as trans form (1222xd(E)). In another mode, it is obtained as a mixture of cis form and trans form.

Furthermore, it is also possible to conduct a further fluorination on 1,2,3-trichloro-3,3-difluoropropene (1222xd) to achieve a conversion into 1,2-dichloro-3,3,3-trifluoropropene (1223xd). Therefore, similar to 1,1,2,3,3-pentachloropropene (1220xa), it is optional to supply the separated 1,2,3-trichloro-3,3-difluoropropene (1222xd) as the reaction raw material to the reaction system. With this, it is possible to efficiently produce 1,2-dichloro-3,3,3-trifluoropropene (1223xd).

In the reaction according to the present invention, the obtained 1,2-dichloro-3,3,3-trifluoropropene (1223xd) exists as liquid under ordinary temperature and ordinary pressure. In one mode of the present invention, 1223xd is obtained as cis form (1223xd(Z)). Alternatively, it is obtained as trans form (1223xd(E)). Alternatively, it is obtained as a mixture of cis form (1223xd(Z)) and transform (1223xd(E)). By conducting a purification operation, such as distillation, on this mixture, it is possible to separate cis form and trans form from each other. With this, it is possible to obtain cis-1,2-dichloro-3,3,3-trifluoropropene (1223xd(Z)) and trans-1,2-dichloro-3,3,3-trifluoropropene (1223xd(E)) of high purities.

<Method for Producing 1,1,2,3,3-Pentachloropropene (1220xa)>

There is shown one example of the method for producing 1,1,2,3,3-pentachloropropene (1220xa), which is used as the raw material in the reaction according to the present invention.

It is preferable to produce 1,1,2,3,3-pentachloropropene (1220xa) by a method comprising at least the step (hereinafter may be referred to as the third step) of dehydrochlorinating 1,1,1,2,3,3-hexachloropropane (230da) in a liquid phase in the presence of a Lewis acid catalyst.

Furthermore, it is preferable to produce 1,1,1,2,3,3-hexachloropropane (230da) by a method comprising at least the step (hereinafter may be referred to as the second step) of chlorinating 1,1,3,3-tetrachloropropene (1230za) by chlorine.

Furthermore, it is preferable to produce 1,1,3,3-tetrachloropropene (1230za) by a method comprising at least the step (hereinafter may be referred to as the first step) of dehydrochlorinating 1,1,1,3,3-pentachloropropane (240fa).

Since 1,1,2,3,3-pentachloropropene (1220xa) is used as the raw material in the reaction according to the present invention, it is preferable to conduct the third step. In contrast with this, the second step provides a method for producing 1,1,1,2,3,3-hexachloropropane (230da), which is the raw material of 1,1,2,3,3-pentachloropropene (1220xa), and the first step provides a method for producing 1,1,3,3-tetrachloropropene (1230za), which is the raw material of 1,1,1,2,3,3-hexachloropropane (230da). The adoption of other methods is not prevented. It is, however, possible to advantageously produce 1,1,1,2,3,3-hexachloropropane (230da) by adopting the second step and/or the first step.

It is particularly preferable to conduct the first step and/or second step in a liquid phase and in the presence of a Lewis acid catalyst in order to advantageously obtain the precursor compound (1230za or 230da).

In the case of conducting the first step, the second step and the third step in this order, it is possible to apply the same Lewis acid catalyst in the three steps. In this case, between the first step and the second step and between the second step and the third step, neither a catalyst separation operation from the reaction mixture nor a catalyst addition operation is necessary. As a result, the reactions of the first step, the second step and the third step can also be one-pot multistep reaction in the presence of the same Lewis acid catalyst to synthesize 1,1,2,3,3-pentachloropropene (1220xa) from 1,1,1,3,3-pentachloropropane (240fa).

As a matter common to all the steps of the first to third steps, water is mentioned. Since water is not positively involved in the reaction in the reactions of the first to third steps, there is no positive reason to add water to the reaction system in the present invention. In particular, in the case of conducting these reactions in the presence of a Lewis acid catalyst, it is preferable to conduct the reactions in a condition that water content is as low as possible (generally referred to as a condition free from water) in order to increase activity of the Lewis acid. However, activity of the Lewis acid is sufficiently maintained, if water exists by about 1 mass % relative to the total mass of the reaction liquid. Therefore, it is desirable to maintain the water content at 1 mass % or less relative to the total mass of the reaction liquid. If the water content is 0.1 mass % or less relative to the total mass of the reaction liquid, it is more preferable.

Furthermore, solvent is not necessary in any reaction of the first to third steps. In the case of conducting these reactions by liquid-phase reaction, each of 1,1,1,3,3-pentachloropropane (240fa), 1,1,3,3-tetrachloropropene (1230za), 1,1,1,2,3,3-hexachloropropane (230da), and 1,1,2,3,3-pentachloropropene (1220xa) as the raw material/the product forms a stable liquid phase by itself, and the target reactions progress in a liquid phase containing these as major components.

Furthermore, as a matter common to all the reactions of the first to third steps, when implementing the present invention, the implementation in the presence of inert gas (nitrogen gas, argon gas, etc.) is not essential. However, if the reaction is conducted with nitrogen gas flow, it may be possible to achieve a smoother reaction, particularly when conducting the reaction on a large scale. Such optimum reaction mode can be suitably set by knowledge of a person skilled in the art.

In the following, each of the first to third steps is explained.

[1] Regarding the First Step

The first step is a step of dehydrochlorinating 1,1,1,3,3-pentachloropropane (240fa) to obtain 1,1,3,3-tetrachloropropene (1230za). 1,1,1,3,3-pentachloropropane (240fa) as the starting raw material of the first step is the starting raw material of 1,1,1,3,3-pentafluoropropane (245fa) and can be synthesized by reacting carbon tetrachloride with vinyl chloride in the presence of catalyst (for example, see U.S. Pat. No. 7,094,936).

As the reaction of the first step, it is possible to adopt either a method (the reaction in gas phase in the absence of catalyst) described in JP Patent 4855550 or a method (the reaction in liquid phase in the presence of a Lewis acid catalyst) described in U.S. Pat. No. 7,094,936. In the method described in JP Patent 4855550, however, a high temperature of around 500° C. is required. Therefore, load on the reactor is generally large. In contrast with this, in the method described in U.S. Pat. No. 7,094,936, the dehydrochlorination reaction progresses smoothly even at around 70° C. Therefore, generally speaking, the method described in U.S. Pat. No. 7,094,936 is more preferable. Thus, in the following explanation, the reaction of the first step in liquid phase in the presence of a Lewis acid catalyst, which is a more preferable mode, is explained.

The reactor is not particularly limited. It is, however, a reaction to generate hydrogen chloride. Therefore, it is preferable to use an acid-proof reactor. Specifically, a reactor made of glass or stainless steel, or one lined with glass or resin is preferable. The reactor is preferably one with a stirring facility and a reflux tower. In the case of conducting the first step and the second step by the same tank, one having a blowing tube capable of introducing chlorine is preferable. Furthermore, in the case of this reaction in liquid phase in the presence of a Lewis acid catalyst, as mentioned hereinafter, it progresses sufficiently if the reaction temperature is 200° C. or lower. This is not necessarily higher than 1,1,1,3,3-pentachloropropane (240fa) boiling point (179° C.) and 1,1,3,3-tetrachloropropene (1230za) boiling point (149° C.). Therefore, if equipped with a reflux tower, it is possible to maintain the reaction mixture in liquid condition under ordinary pressure, and it is possible to conduct the reaction under ordinary pressure (open system). However, a method to conduct the reaction by using a pressurized reactor while hydrogen chloride to be generated is timely purged is not prevented, either.

The Lewis acid catalyst is exemplified by metal halides. The metal halide refers to one having a bond between the metal atom and the halogen atom. One that a bond between the metal atom and the halogen atom is confirmed by IR, XRD, XPS, etc. can be used as the catalyst of the present invention. Specifically, there is preferable a halide of at least one metal selected from the group consisting of aluminum, vanadium, chromium, manganese, iron, cobalt, nickel, copper, zirconium, niobium, molybdenum, ruthenium, rhodium, palladium, silver, tin, antimony, tantalum, and tungsten. Of these, a chloride is preferable. A chloride of at least one metal selected from the group consisting of aluminum, iron, tin and antimony is particularly preferable. Aluminum chloride and iron chloride are still more preferable. In the case of iron chloride, ferric chloride is preferable. Anhydrous catalyst is preferable, due to its high catalytic activity. A commercial anhydride may be used as it is, but it is also possible to obtain an anhydride by treating a hydrate with thionyl chloride.

When conducting the first step in liquid phase in the presence of a Lewis acid catalyst (may be referred to as the first Lewis acid catalyst), it is easy to directly use a metal halide as the Lewis acid catalyst. If a person skilled in the art desires, it is also possible to previously conduct a hydrogen chloride treatment on these metals' nitrates, carbonates, etc. and zero-valent metal powder, thereby leading to an active metal halide that can be used as a Lewis acid catalyst. It is also possible to convert a zero-valent metal powder, nitrate, etc. to a chloride high in activity by hydrogen chloride that is generated by the dehydrochlorination reaction of 1,1,1,3,3-pentachloropropane (240fa).

Although the optimum value of the amount of the Lewis acid catalyst (the first Lewis acid catalyst) varies depending on the catalyst type and/or the operational condition such as reaction temperature, it is 0.01 to 10 mol %, more preferably 0.1 to 5 mol %, relative to the organic matter as the raw material. If it is less than this, the reaction rate becomes slow to lower productivity. Therefore, it is not preferable. If it is greater this, not only resource becomes waste, but also an unexpected side reaction(s) may occur.

In the case of conducting the reaction of the first step in liquid phase in the presence of a Lewis acid catalyst, the reaction temperature is normally 40 to 200° C., more preferably 45 to 120° C. The optimum temperature depends a little on the type of the Lewis acid catalyst. In the case of aluminum chloride, 40 to 100° C. (typically 50 to 80° C.) is particularly preferable. To be a little higher than this, 70 to 110° C. (typically 70 to 80° C.) is particularly preferable in the case of ferric chloride. If it is lower than these ranges, the reaction rate may become slow to lower productivity. If it is higher than those, the production of high-boiling-point by-products may increase to lower selectivity of 1,1,3,3-tetrachloropropene (1230za).

As a preferable reaction example, it is possible to cite a method in which a reactor that is made of glass or lined with glass is charged with the catalyst and 240fa, followed by heating with stirring, and then only the resulting hydrogen chloride is discharged by a reflux tower with water (tap water, industrial water, etc.) flowing therethrough.

In the case of conducting the first step by such liquid-phase reaction, the liquid phase in the inside of the reactor is replaced with 1,1,3,3-tetrachloropropene (1230za) as the target, as time passes. As measuring the progress of the reaction by gas chromatography etc., it is preferable to terminate the reaction when 1,1,1,3,3-pentachloropropane (240fa) was almost consumed.

As mentioned above, the reaction of the first step is not prevented from its implementation in gas-phase in the absence of catalyst. In the case of this no-catalyst reaction, the reaction temperature becomes normally 350 to 550° C. Due to high temperature, load on the apparatus becomes generally large. Since it is a flow-type reaction, it may become advantageous in the case of producing 1,1,3,3-tetrachloropropene (1230za) on a large scale. This method is, however, a no-catalyst method. Therefore, if this method is adopted as the first step, it contradicts a particularly preferable 1,1,2,3,3-pentachloropropene (1220xa) production mode to conduct the first to third steps in liquid phase by a one-pot multistep reaction using a common Lewis acid catalyst.

1,1,3,3-tetrachloropropene (1230za) synthesized by the first step can be used as the raw material of the subsequent second step, without conducting a post treatment such as the catalyst separation and distillation purification. Implementing catalyst separation and/or distillation purification is not prevented, but the point that the steps can be conducted in succession without conducting these treatments is also one of great merits of the present invention. Therefore, it is one preferable mode to conduct no such post-treatment.

[2] Regarding the Second Step

The second step is a step of chlorinating 1,1,3,3-tetrachloropropene (1230za) by chlorine (Cl) into 1,1,1,2,3,3-hexachloropropane (230da).

As the reaction of the second step, the above-mentioned JP Patent 4855550 discloses the following two methods of (a) a reaction in gas phase in the absence of catalyst and (b) a reaction in liquid phase in the absence of catalyst. Either one can be adopted to conduct the second step.

However, the present inventors have found another method as the method of the second step, that is, (c) a reaction in liquid phase in the presence of Lewis acid catalyst, and a fact that the reaction rate of the second step increases even at lower temperatures by adopting this method (c). As a result, it became possible to efficiently produce 1,1,1,2,3,3-hexachloropropane (230da) while by-production of impurities in the second step was difficult to happen. Thus, herein, the method (c) is explained in detail.

In the case of conducting the reaction of the second step by the method (c), the reaction progresses by bubbling chlorine gas ($Cl_2$) into 1,1,3,3-tetrachloropropene (1230za) in liquid state in the presence of a Lewis acid catalyst (may be referred to as the second Lewis acid catalyst). It is possible to use 1,1,3,3-tetrachloropropene (1230za) as the raw material as it is, without purifying the product of the first step. Using 1,1,3,3-tetrachloropropene (1230za) produced by another method or separately purified to high purity is not prevented, either.

Material of the reactor (reaction apparatus) is not particularly limited. Due to the use of strongly oxidizing chlorine gas, one made of glass or stainless steel is preferable. Furthermore, a reaction lined with glass or resin is also preferable. Furthermore, the reactor is preferably one equipped with a blowing tube, a stirring facility and a reflux tower. It is also possible to use a reaction tank having the same specification as that of the first step.

In the case of conducting the reaction of the second step, the Lewis acid catalyst (the second Lewis acid catalyst) is exemplified by metal halides. The metal halide refers to one having a bond between the metal atom and the halogen atom. One that a bond between the metal atom and the halogen atom is confirmed by IR, XRD, XPS, etc. can be used as the catalyst of the present invention. Specifically, there is preferable a halide of at least one metal selected from the group consisting of aluminum, vanadium, chromium, manganese, iron, cobalt, nickel, copper, zirconium, niobium, molybdenum, ruthenium, rhodium, palladium, silver, tin, antimony, tantalum, and tungsten. Of these, a chloride is preferable. A chloride of at least one metal selected from the group consisting of aluminum, iron, tin and antimony is particularly preferable. Aluminum chloride and iron chloride are still more preferable. In the case of iron chloride, ferric chloride is preferable. Anhydrous catalyst is preferable, due to its high catalytic activity. A commercial anhydride may be used as it is, but it is also possible to obtain an anhydride by treating a hydrate with thionyl chloride.

When conducting the second step in liquid phase in the presence of a Lewis acid catalyst, it is easy to directly use a metal halide as the Lewis acid catalyst. If a person skilled in the art desires, it is also possible to previously conduct a hydrogen chloride treatment on these metals' nitrates, carbonates, etc. and zero-valent metal powder, thereby leading to an active metal halide that can be used as a Lewis acid catalyst. Similar to the first step, it is also possible to convert a zero-valent metal powder, nitrate, etc. to a chloride high in activity by hydrogen chloride.

Although the optimum value of the amount of the Lewis acid catalyst varies depending on the catalyst type and/or the operational condition such as reaction temperature, 0.01 to 10 mol %, more preferably 0.1 to 5 mol %, is recommended relative to the organic matter as the raw material. If it is less than this, the reaction rate becomes slow to lower productivity. Therefore, it is not preferable. If it is greater this, not only resource becomes waste, but also an unexpected side reaction(s) may occur.

As already mentioned, in case that the first step is conducted in the presence of a Lewis acid catalyst (the first Lewis acid catalyst) and then the second step is conducted subsequently to the first step, it is also possible to reuse the Lewis acid catalyst (the first Lewis acid catalyst), which has been used in the first step, as the second step's Lewis acid catalyst (the second Lewis acid catalyst), without its separation and recovery from the system. In this case, it is not necessary to newly add a Lewis acid catalyst in the second step. However, for the purpose of further increasing the reaction rate, adding a Lewis acid catalyst in the second step is not prevented, either.

In the case of conducting the second step in liquid phase in the presence of the Lewis acid catalyst, the reaction temperature is preferably −20 to +110° C., more preferably 0 to 60° C. If it is lower than this range, the reaction rate may become slow to lower productivity. If it is higher than this, by-production of impurities may increase to lower selectivity of 1,1,1,2,3,3-hexachloropropane (230da). As mentioned above, in the case of conducting the second step at a too-high temperature or for a too-long period of time, by-production of high-boiling-point impurities is found significantly (selectivity on gas chromatograph is also lowered). In order to prevent the formation of such impurities as much as possible, in the second step, it is desirable to conduct the reaction at a temperature as low as possible in a range that the target reaction progresses at a sufficient rate, and such temperature can be optimized by knowledge of a person skilled in the art in accordance with the catalyst amount and other conditions.

In the case of conducting the second step in the presence of the Lewis acid catalyst, it progresses sufficiently in many cases if the reaction temperature is lower than that in the case of conducting the first step in the presence of the Lewis acid catalyst. Therefore, it is preferable to conduct the second step at a temperature lower than that of the first step.

Furthermore, in the case of conducting the second step in the presence of the Lewis acid catalyst, it progresses sufficiently in many cases if the reaction temperature is lower than that in the case of conducting the after-mentioned third step in the presence of the Lewis acid catalyst. Therefore, it is preferable to conduct the second step at a temperature lower than that of the third step. In particular, the reaction of the third step originally can progress in parallel with the reaction of the second step. If the reaction of the second step is intentionally conducted at a low temperature to the extent that the reaction of the third step does not progress significantly, in many cases, the formation of the above-mentioned impurities can be suppressed, and it is easier to conduct the process control.

As a preferable example in the case of conducting the second step by the method (c), it is possible to cite a method in which a reactor made of glass or lined with glass is charged with the catalyst and 1,1,3,3-tetrachloropropene (1230za), chlorine gas is bubbled thereinto through a blowing tube with stirring, and only organic matter is refluxed and only the unreacted gas is discharged by a reflux tower with water (tap water, industrial water, etc.) flowing therethrough. When conducting the second step by the method (c), conducting the reaction by introducing chlorine gas into a sealed-type reactor is not prevented, either. It is, however, an exothermic reaction, and the reaction progresses at a relatively high rate. Therefore, care is necessary for controlling the reaction.

Conducting the reaction of the method (c) under pressurization by using a pressure-proof vessel is not prevented, either. As mentioned above, however, in the case of conducting the second step by this method, the reaction temperature is sufficiently low. Therefore, in general, it is easy and preferable to conduct the reaction under an ordinary pressure condition.

If a person in the same field desires, it is also possible to conduct a light (ultraviolet ray) irradiation in order to accelerate the chlorination reaction. Furthermore, adding a radical initiator is also possible, but it is not necessary in particular. In the case of such addition, it may become cumbersome to separate the radical initiator and the product from each other at last.

In the second step, 1,1,3,3-tetrachloropropene (1230za) of the liquid phase in the inside of the reactor turns into the target 1,1,1,2,3,3-hexachloropropane (230da) as time passes. As the progress of the reaction is measured by gas chromatography, etc., it is preferable to terminate the reaction when the raw material 1,1,3,3-tetrachloropropene (1230za) has been almost consumed.

As mentioned above, as the second step, (a) the reaction in gas phase in the absence of catalyst or (b) the reaction in liquid phase in the absence of catalyst is not prevented, either.

In the case of (a), it is possible in general to adopt a reaction temperature from boiling point (about 149° C.) of 1,1,3,3-tetrachloropropene (1230za) to 280° C. In the case of (b), it is possible in general to adopt a reaction temperature of 50 to 120° C.

In the case of adopting the method (a), if 1,1,3,3-tetrachloropropene (1230za) is exposed to high temperatures for a long time, the production of impurities tends to increase. Therefore, it is preferable to adjust the reaction time (heating time) by the optimization of a person skilled in the art (preferably around 1 to 40 seconds). In the case of adopting the method (a), load on the apparatus becomes large in general, but, due to a flow-type reaction, it may be advantageous in the case of producing 1,1,1,2,3,3-hexachloropropane (230da) on a large scale. However, if this method is adopted, it contradicts a particularly preferable 1,1,2,3,3-pentachloropropene (1220xa) production mode to conduct the first to third steps in liquid phase by a one-pot multistep reaction using the same catalyst.

On the other hand, in the case of adopting the method (b), as compared with the above-mentioned method (c), at first sight, it seems that there is no difference in preferable temperature range. However, as compared with the method (c), there is a tendency that it requires a longer reaction time at the same temperature, and high-boiling-point impurities tend to be formed in the method (b). Furthermore, due to the reaction in the absence of catalyst, it also contradicts a particularly preferable 1220xa production mode to conduct the first to third steps in liquid phase by a one-pot multistep reaction.

Therefore, as the second step, as mentioned above, it is particularly preferable to adopt the method (c) (the reaction in liquid phase in the presence of Lewis acid catalyst).

1,1,1,2,3,3-hexachloropropane (230da) synthesized by the second step can be used as the raw material of the subsequent third step, without conducting a post treatment such as the catalyst separation and distillation purification. Implementing catalyst separation and/or distillation purification is not prevented, but the point that the steps can be conducted in succession without conducting these treatments is also one of great merits of the present invention. Therefore, it is one preferable mode to conduct no such post-treatment.

[3] Regarding the Third Step

The third step is a step of dehydrochlorinating 1,1,1,2,3,3-hexachloropropane (230da) in liquid phase in the presence of a Lewis acid catalyst (the third Lewis acid catalyst) to obtain 1,1,2,3,3-pentachloropropene (1220xa).

The third step progresses by heating 1,1,1,2,3,3-hexachloropropane (230da) in liquid phase in the presence of a Lewis acid catalyst. The reactor is not particularly limited. However, since hydrogen chloride is generated, on made of glass or stainless steel is preferable. Of course, a reactor lined with glass or resin is also preferable. The reactor is preferably one having a stirring facility and a reflux tower.

It is also possible to continuously use the same reactor as that of the second step. In the third step too, it is also possible to continuously use the reactor that has a blowing tube capable of introducing chlorine and that has been preferably adopted in the second step. In this case, it is not necessary to replace the chlorine gas, which has been introduced into the system in the second step, with an inert gas. Even in a condition that chlorine gas remains, the reaction of the third step itself progresses with no problem. In contrast with this, in the case of using a reactor that is different from the reactor of the second step, it is also an effective method to conduct the third step after replacing the chlorine gas with an inert gas.

The Lewis acid catalyst (the third Lewis acid catalyst) used in the third step is exemplified by metal halides. The metal halide refers to one having a bond between the metal atom and the halogen atom. One that a bond between the metal atom and the halogen atom is confirmed by IR, XRD, XPS, etc. can be used as the catalyst of the present invention. Specifically, there is preferable a halide of at least one metal selected from the group consisting of aluminum, vanadium, chromium, manganese, iron, cobalt, nickel, copper, zirconium, niobium, molybdenum, ruthenium, rhodium, palladium, silver, tin, antimony, tantalum, and tungsten. Of these, a chloride is preferable. A chloride of at least one metal selected from the group consisting of aluminum, iron, tin and antimony is particularly preferable. Aluminum chloride and iron chloride are still more preferable. In the case of iron chloride, ferric chloride is preferable. Anhydrous catalyst is preferable, due to its high catalytic activity. A commercial anhydride may be used as it is, but it is also possible to obtain an anhydride by treating a hydrate with thionyl chloride.

When conducting the third step, it is easy to directly use a metal halide as the Lewis acid catalyst. If a person skilled in the art desires, it is also possible to previously conduct a hydrogen chloride treatment on these metals' nitrates, carbonates, etc. and zero-valent metal powder, thereby leading to an active metal halide that can be used as a Lewis acid catalyst. Similar to the first step and the second step, it is also possible to convert a zero-valent metal powder, nitrate, etc. to a chloride high in activity by hydrogen chloride.

Although the optimum value of the amount of the Lewis acid catalyst in the third step varies depending on the catalyst type and/or the operational condition such as reaction temperature, it is 0.01 to 10 mol %, more preferably 0.1 to 5 mol %, relative to the organic matter as the raw material. If it is less than this, the reaction rate becomes slow to lower productivity. Therefore, it is not preferable. If it is greater this, not only resource becomes waste, but also an unexpected side reaction(s) may occur.

The reaction temperature is normally preferably 50 to 200° C., more preferably 70 to 150° C. If it is lower than this range, the reaction rate may become slow to lower the productivity. If it is higher than this, by-production of high-boiling-point substances may increase to lower selectivity of 1,1,2,3,3-pentachloropropene (1220xa). The reaction of the third step is different in optimum temperature depending on the type of Lewis acid used. In the case of aluminum chloride, it is 70 to 110° C. In the case of ferric chloride, it is somewhat higher than this and is 100 to 150° C.

As a preferable reaction example, it is possible to cite a method in which a reactor made of glass or lined with glass is charged with the Lewis acid catalyst and liquid of 1,1,1,2,3,3-hexachloropropane (230da), followed by heating with stirring under ordinary pressure. As the reaction starts, hydrogen chloride is generated. Therefore, it is possible to discharge hydrogen chloride by a reflux tower with tap water, etc. flowing therethrough. A method in which the reaction is conducted by using a pressure-proof reactor while the generated hydrogen chloride gas is timely discharged or purged is not prevented, either. In the present step, however, the reaction progresses sufficiently at a temperature that is sufficiently lower than boiling points of the raw material and the product. Therefore, in general, it is easy and preferable to conduct the reaction under ordinary pressure.

In the third step, 1,1,1,2,3,3-hexachloropropane (230da) of the liquid phase of the inside of the reactor turns into 1,1,2,3,3-pentachloropropene (1220xa) as time passes. As the progress of the reaction is measured by gas chromatography, etc., it is preferable to terminate the reaction when 1,1,1,2,3,3-hexachloropropane (230da) has been almost consumed.

[4] Regarding One-Pot Multistep Reaction

A particularly preferable mode when conducting the present invention is a mode in which (not only in the third step), but also in the first step and the second step, the reactions are conducted in liquid phase in the presence of a Lewis acid catalyst, in which the Lewis acid catalyst (the first Lewis acid catalyst and the second Lewis acid catalyst) is the same type as that of the Lewis acid catalyst (the third Lewis acid catalyst) used in the third step, and in which the catalyst is not separated from the reaction mixture between the first step and the second step and between the second step and the third step, resulting in reusing the Lewis acid catalyst (the first Lewis acid catalyst) itself, which has been used in the first step, in the second step and the third step. With this, it is possible to reuse the Lewis acid catalyst itself, which has been used in the first step, in the second step and the third step. Therefore, it is possible to not only save the catalyst, but also extremely simplify the reaction steps.

According to desire of a person skilled in the art, using the same Lewis acid catalyst only in the first step and the second step or only in the second step and the third step is not prevented, either. However, the most preferable one is an embodiment in which it is conducted in liquid phase by reusing the same Lewis acid catalyst from the first step to the third step.

In the present specification, such embodiment is referred to as a one-pot multistep reaction. In general, in order to improve operability, there is a proposal of a one-pot multistep reaction in which a plurality of steps are conducted in the same reaction tank without isolating the product. However, a one-pot multistep reaction in which all of the steps are catalytic reactions and the same catalyst is used therein is rare. In the present invention, specifically, it is possible to use the same catalyst in the three steps. In particular, aluminum chloride ($AlCl_3$) or ferric chloride ($FeCl_3$), which has a low price and a good availability and shows superior selectivity and reaction rate throughout the three steps, is recommended as a particularly superior common catalyst. There are known two-types of iron chloride, that is, ferrous chloride ($FeCl_2$) and ferric chloride ($FeCl_3$). In the present invention, ferric chloride is superior due to its higher catalytic activity.

In particular, ferric chloride is easy in handling and has a good reactivity. Therefore, it is a particularly preferable common catalyst.

Since the products of the first step and the third step are reductive unsaturated compounds, it may happen that catalyst valency (oxidation condition of the catalyst active center element (e.g., iron)) lowers to lower activity. However, as the present inventors examined the one-pot multistep reaction from the first step to the third step, a significant lowering of the catalytic activity was not found. The reason of this is not clear, but it can be considered as one interpretation (assumption), as follows. That is, in the case of supplying the reaction mixture and the catalyst of the first step to the second step without their separation, even if valency of a part of the catalyst lowers in the first step, chlorine ($Cl_2$) having a high oxidative power restores valency of the Lewis acid catalyst to achieve a high catalytic activity condition. Therefore, the second step progresses under a high catalytic activity. If continuously conducting the third step, the third step also progresses under a high catalytic activity. It is believed that the above interpretation is possible.

As an example of particularly preferable embodiments, a glass-made reaction tank having a stirrer, a reflux tower, a stirrer and a blowing tube is charged with 1,1,1,3,3-pentachloropropane (240fa) and iron chloride, followed by heating at 70 to 110° C. (typically 70 to 90° C.) with stirring and discharging the generated hydrogen chloride via the reflux tower to conduct the first step. As measuring composition of the reaction mixture by gas chromatography, the first step is continued until conversion reaches, for example, 95% or higher. After that, while stirring was continued, the reaction mixture was cooled. When temperature of the reaction mixture lowers to 0 to 60° C., which is suitable for conducting the second step, chlorine is bubbled to conduct the second step at a predetermined temperature (e.g., 30 to 50° C.) of 0 to 60° C. The second step is continued until conversion reaches, for example, 95% or higher. After that, supply of chlorine is stopped, and the reaction temperature is raised to 110 to 130° C. to conduct the third step. The third step is continued until conversion reaches, for example, 95% or higher. The reaction of the second step and the reaction of the third step have characters that they originally can progress in parallel with each other. However, in the case of using aluminum chloride or ferric chloride as the Lewis acid catalyst, in many cases, there is a clear difference between the temperature promoting the reaction of the second step and the temperature promoting the reaction of the third step. Therefore, it becomes possible to make the second step and the third step progress separately by setting the reaction temperature of the second step to be relatively low and by setting the reaction temperature of the third step to be higher than this at least, as mentioned above. If the two reactions are separately conducted in this manner, it is possible to efficiently produce the target 1,1,2,3,3-pentachloropropene (1220xa) while easily suppressing the generation of impurities.

In the present invention, using a plurality of Lewis acid catalysts together (they are added at the same time to be used as the catalyst) as the Lewis acid catalyst in each step is not prevented. It is, however, normal that different Lewis acid catalysts generally cause different reaction optimum temperatures. That is, if different Lewis acid catalysts are used together, the optimum temperature of each step becomes wide. As a result, it becomes difficult to obtain the temperature selectivity between the reactions of the second and third steps, and the second step and the third step tend to progress at the same time. Therefore, in the present invention, it is particularly preferable to consistently use a single type of the Lewis acid catalyst.

In the present invention, "one-pot" does not limit the number of reactors, but also refers to proceeding to the next step without separating the reaction product and the catalyst. That is, depending on the facility of a person skilled in the art, not only it is possible to conduct the three steps by a single tank (reactor), but also when having a plurality of tanks it is possible to adopt a method in which, after completing the first step, the product and the catalyst are transferred to another tank without their separation to conduct the second step, and then, after completing the second step, the product and the catalyst are transferred to another tank without their separation to conduct the third step. Upon this, it is also possible to efficiently cool or heat the reaction product and the catalyst through a heat exchanger, when transferring the reaction product and the catalyst from the tank of the first step to that of the second step or from the tank of the second step to that of the third step.

After completing the third step, it is possible to easily separate the catalyst and the organic matter from each other by distillation. Of course, it is possible to isolate 1,1,2,3,3-pentachloropropene (1220xa) of high purity by rectification. The obtained 1,1,2,3,3-pentachloropropene (1220xa) can also be subjected to washing with water and drying. In the case of conducting washing with water and drying, it is preferable to conduct them prior to distillation.

EXAMPLES

The 1,2-dichloro-3,3,3-trifluoropropene (1223xd) production method of the present invention is explained by the following examples, but the present invention is not limited by the following examples.

In the explanation, FID % refers to areal % when analyzed with a gas chromatograph equipped with FID as the detector.

Example 1-1

A 300-mL stainless steel autoclave equipped with a condenser with a 20° C. cooling liquid circulating therethrough and a pressure gauge was charged with 60 g (0.28 mol) of 1,1,2,3,3-pentachloropropene (1220xa) and 111.9 g (5.59 mol) of hydrogen fluoride (the molar ratio of 1220xa/hydrogen fluoride=about 1/20), followed by heating the autoclave to 150° C. At the time when pressure exceeded about 4 MPaG, the reaction product gas was drawn out of a needle valve at an exit of the condenser to maintain 4.0 to 4.5 MPaG. The drawn-out gas was passed through a fluororesin-made gas washing bottle containing iced water therein, which was cooled in an iced water bath, thereby absorbing acid and then recovering the reaction product organic matter by a glass trap in dry-ice/acetone bath. 3 hours after the start of the temperature increase, no observation of the pressure increase was confirmed, and then the reactor was purged. The drawn-out gas was recovered by the fluororesin-made gas washing bottle containing iced water therein, which was cooled in an iced water bath, and the glass trap in dry-ice/acetone bath. After cooling the reactor, the reaction liquid in the autoclave and the glass trap recovery in dry-ice/acetone bath were all mixed in the fluororesin-made gas washing bottle containing iced water therein. The combined mixed solution was transferred into a fluororesin-made separatory funnel, and then its organic matter was recovered by separation from the aqueous layer. The amount of this recovered organic matter was 42.7 g.

As composition of the recovered organic matter was analyzed by gas chromatography, it was found that Z-1,2-dichloro-3,3,3-trifluoropropene (Z-1223xd) was 88.6 FID %, E-1,2-dichloro-3,3,3-trifluoropropene (E-1223xd) was 0.7 FID %, 1,1,2,3,3-pentachloropropene (1220xa) was not detected, 1,2,3-trichloro-3,3-difluoropropene (1222xd) was 9.8 FID %, and others were 0.9 FID %. Yield was 83.8%.

Example 1-2

The reaction was conducted in the same manner as in Example 1, except in that 56 g (2.80 mol) of the raw material hydrogen fluoride (the molar ratio of 1220xa/hydrogen fluoride=about 1/10) was used and that the reaction temperature was set at 120° C.

As composition of the reaction liquid was analyzed by gas chromatography, it was found that Z-1,2-dichloro-3,3,3-trifluoropropene (Z-1223xd) was 33.8 FID %, E-1,2-dichloro-3,3,3-trifluoropropene (E-1223xd) was not detected, 1,1,2,3,3-pentachloropropene (1220xa) was 0.1 FID %, 1,2,3-trichloro-3,3-difluoropropene (1222xd) was 62.3 FID %, and others were 3.8 FID %. Yield was 29.4%.

Preparation Example 1

Preparation of Fluorinated γ-Alumina Catalyst

A cylindrical, stainless steel (SUS316L) reaction tube equipped with an electric furnace and having a diameter of 2.5 cm and a length of 30 cm was charged with 110 mL of a granular γ-alumina, followed by heating the inside of the reaction tube until 200° C. while nitrogen gas was allowed to flow. At the time when no discharge of water vapor from the reaction tube was found, the nitrogen gas was accompanied by hydrogen fluoride (HF), and its concentration was gradually increased. At the time when the hot spot caused by fluorination of the granular γ-alumina reached the outlet end of the reaction tube, the temperature of the reaction tube was stepwise increased by 100° C., maintained at each step's temperature for 1 hour, finally increased to 400° C., and maintained under this condition for 1 hour, thereby preparing a γ-alumina catalyst subjected to a fluorination treatment.

Preparation Example 2

Preparation of a Fluorinated Chromia Catalyst

Preparation Example 1 was repeated, except in that the reaction tube was charged with a granular chromia, in place of the granular γ-alumina, thereby preparing a chromia catalyst subjected to a fluorination treatment.

Preparation Example 3

Preparation of a Fluorinated Chromium-Supported Activated Carbon Catalyst

A 20 mass % chromium chloride aqueous solution was prepared in an Erlenmeyer flask, 110 mL of activated carbon was immersed therein, and it was maintained for 3 hours. This activated carbon was filtered and then dried under reduced pressure at 70° C. by using a rotary evaporator, thereby preparing a chromium chloride-supported activated carbon. Then, a cylindrical, stainless steel (SUS316L) reaction tube equipped with an electric furnace and having a diameter of 2.5 cm and a length of 30 cm was charged with 100 mL of the chromium chloride-supported activated carbon, followed by heating the inside of the reaction tube until 200° C. while nitrogen gas was allowed to flow. At the time when no discharge of water vapor from the reaction tube was found, the nitrogen gas was accompanied by hydrogen fluoride (HF), and its concentration was gradually increased. At the time when the hot spot caused by fluorination of the chromium chloride-supported activated carbon reached the outlet end of the reaction tube, the temperature of the reaction tube was stepwise increased by 100° C., maintained at each step's temperature for 1 hour, finally increased to 400° C., and maintained under this condition for 1 hour, thereby preparing a chromium-supported activated carbon catalyst subjected to a fluorination treatment.

Example 2-1

100 mL of the catalyst prepared by Preparation Example 1 was put into a cylindrical, stainless steel (SUS316L) reaction tube equipped with an electric furnace and having a diameter of 2.5 cm and a length of 30 cm, followed by increasing temperature of the inside of the reaction tube to 250° C. while nitrogen gas was allowed to flow. There, vaporized hydrogen fluoride and 1,1,2,3,3-pentachloropropene (1220xa) were introduced at flow rates (speed) shown in Table 1, and the nitrogen gas was stopped when the flow rates became stable. After that, the product gas flowing out of the reactor was passed through a fluororesin-made gas washing bottle containing iced water to remove acid gas and collect the reaction product. Composition of its organic matter recovered by separation from the aqueous layer by a fluororesin-made separatory funnel was analyzed by gas chromatography. The results are shown in Table 2.

Example 2-2 to Example 2-4

Similar to Example 2-1, the reaction was conducted, and the organic matter was recovered from the reaction product, except in that the conditions (reaction temperature, contact time, reaction materials flow rates, and reaction materials molar ratio) shown in Table 1 were modified. The results obtained by analyzing composition of the recovered organic matter by gas chromatography are each shown in Table 2.

Example 2-5

100 mL of the catalyst prepared by Preparation Example 2 was put into a cylindrical, stainless steel (SUS316L) reaction tube equipped with an electric furnace and having a diameter of 2.5 cm and a length of 30 cm, followed by increasing temperature of the inside of the reaction tube to 250° C. while nitrogen gas was allowed to flow. There, at flow rates (speeds) shown in Table 1, the previously vaporized hydrogen fluoride and chlorine were introduced. Then, the previously vaporized 1,1,2,3,3-pentachloropropene (1220xa) was introduced. When the flow rate became stable, the nitrogen gas was stopped. After that, the product gas flowing out of the reactor was passed through a fluororesin-made gas washing bottle containing iced water to remove acid gas and collect the reaction product. Composition of its organic matter recovered by separation from the aqueous layer by a fluororesin-made separatory funnel was analyzed by gas chromatography. The results are shown in Table 2.

Example 2-6

100 mL of the catalyst prepared by Preparation Example 3 was put into a cylindrical, stainless steel (SUS316L) reaction tube equipped with an electric furnace and having a diameter of 2.5 cm and a length of 30 cm, followed by increasing temperature of the inside of the reaction tube to 250° C. while nitrogen gas was allowed to flow. There, at flow rates (speeds) shown in Table 1, the previously vaporized hydrogen fluoride and chlorine were introduced. Then, the previously vaporized 1,1,2,3,3-pentachloropropene (1220xa) was introduced. When the flow rate became stable, the nitrogen gas was stopped. After that, the product gas flowing out of the reactor was passed through a fluororesin-made gas washing bottle containing iced water to remove acid gas and collect the reaction product. Composition of its organic matter recovered by separation from the aqueous layer by a fluororesin-made separatory funnel was analyzed by gas chromatography. The results are shown in Table 2.

Example 2-7

100 mL of Raschig rings (5φ×5 mm) made of SUS316L was put into a cylindrical, stainless steel (SUS316L) reaction tube equipped with an electric furnace and having a diameter of 2.5 cm and a length of 30 cm, followed by increasing temperature of the inside of the reaction tube to 250° C. while nitrogen gas was allowed to flow. There, the vaporized hydrogen fluoride was introduced at a flow rate (speed) shown in Table 1. Then, the previously vaporized 1,1,2,3,3-pentachloropropene (1220xa) was introduced. When the flow rate became stable, the nitrogen gas was stopped. After that, the product gas flowing out of the reactor was passed through a fluororesin-made gas washing bottle containing iced water to remove acid gas and collect the reaction product. Composition of its organic matter recovered by separation from the aqueous layer by a fluororesin-made separatory funnel was analyzed by gas chromatography. The results are shown in Table 2.

Example 2-8

100 mL of Raschig rings (5φ×5 mm) made of SUS316L was put into a cylindrical, stainless steel (SUS316L) reaction tube equipped with an electric furnace and having a diameter of 2.5 cm and a length of 30 cm, followed by increasing temperature of the inside of the reaction tube to 250° C. while nitrogen gas was allowed to flow. There, at a flow rate (speed) shown in Table 1, the previously vaporized hydrogen fluoride was introduced. Then, the previously vaporized 1,1,2,3,3-pentachloropropene (1220xa) was introduced. When the flow rate became stable, the nitrogen gas was stopped. After that, the product gas flowing out of the reactor was passed through a fluororesin-made gas washing bottle containing iced water to remove acid gas and collect the reaction product. Composition of its organic matter recovered by separation from the aqueous layer by a fluororesin-made separatory funnel was analyzed by gas chromatography. The results are shown in Table 2.

The reaction conditions (reaction temperature, contact time, reaction materials flow rates, and reaction materials molar ratio) of Examples 2-1 to 2-8 are summarized in Table 1. The results obtained by analyzing the raw material 1220xa used in Examples 2-1 to 2-8 and composition of the recovered organic matter are shown in Table 2. The raw material 1220xa in Examples 2-1 to 2-8 was prepared by a method similar to the after-mentioned Examples 6-a to 6-c and then by purification through distillation.

TABLE 1

| Example | Reaction temp. [° C.] | Contact time (s) | Flow rate [g/min] | | | Molar ratio | | |
|---|---|---|---|---|---|---|---|---|
| | | | Raw material 1220xa | HF | Cl$_2$ | Raw material 1220xa | HF | Cl$_2$ |
| 2-1 | 250 | 45 | 0.206 | 0.101 | 0 | 1 | 5.3 | 0 |
| 2-2 | 250 | 59 | 0.083 | 0.082 | 0.0016 | 1 | 11.7 | 0.0059 |
| 2-3 | 250 | 32 | 0.312 | 0.138 | 0.0016 | 1 | 4.7 | 0.016 |
| 2-4 | 220 | 46 | 0.208 | 0.098 | 0.0016 | 1 | 5.0 | 0.023 |
| 2-5 | 250 | 44 | 0.220 | 0.102 | 0.0016 | 1 | 5.0 | 0.022 |
| 2-6 | 250 | 44 | 0.208 | 0.101 | 0.0016 | 1 | 5.2 | 0.023 |
| 2-7 | 250 | 58 | 0.158 | 0.078 | 0 | 1 | 5.3 | 0 |
| 2-8 | 250 | 30 | 0.311 | 0.151 | 0 | 1 | 5.2 | 0 |

TABLE 2

| Example | GC analysis result [FID %] | | | | | |
|---|---|---|---|---|---|---|
| | 1224 | 1223xd(Z) | 1223xd(E) | 1222xd | 1220xa | Others |
| Raw material 1220xa | — | — | — | — | 99.2 | 0.8 |
| 2-1 | 0.2 | 95.8 | 3.0 | 0.2 | <0.1 | 0.7 |
| 2-2 | 0.6 | 95.1 | 2.9 | 0.1 | <0.1 | 1.3 |
| 2-3 | 0.3 | 95.6 | 2.8 | 0.6 | <0.1 | 0.7 |
| 2-4 | 0.2 | 94.4 | 1.7 | 2.8 | <0.1 | 0.8 |
| 2-5 | 0.2 | 95.4 | 2.9 | 0.2 | <0.1 | 1.2 |
| 2-6 | 0.3 | 95.8 | 2.9 | 0.1 | <0.1 | 0.8 |
| 2-7 | 0.1 | 75.9 | 1.2 | 21.0 | 0.2 | 1.6 |
| 2-8 | <0.1 | 27.0 | 0.4 | 60.5 | 2.3 | 9.8 |

In Table 2, "—" indicates no detection.
In Table 2, 1224 represents chlorotetrafluoropropene.

Example 3-1

First Step (Dehydrochlorination of 1,1,1,3,3-Pentachloropropane (240fa))

A 100-mL three-necked flask equipped with a ball filter, a thermometer, a Dimroth condenser that allows tap water to flow therethrough, and a stirrer was charged with 50.02 g (0.23 mol) of 1,1,1,3,3-pentachloropropane (240fa) having a purity of 98.3 FID % and 0.93 g (0.006 mol) of ferric chloride, and then stirring was started. It was connected by using a PFA tube at an upper part of the Dimroth condenser to an empty trap of a 500-mL PFA container and then a 500-mL PFA container charged with 250 g of sodium hydroxide aqueous solution having a concentration of 25 weight %. While nitrogen was introduced through the ball filter at a flow rate of 5 mL/minute, the flask was heated to 80° C. in an oil bath. The reaction was conducted for 4 hours, and it was analyzed by gas chromatography. With this, 1,1,1,3,3-pentachloropropane (240fa) was 2.8 FID %, 1,1,3,3-tetrachloropropene (1230za) was 92.8 FID %, and others were 4.3 FID % (see Table 1).

Examples 3-2 to 3-6

First Step

Similar to Example 3-1, the reaction of the first step was conducted by changing the catalyst, the catalyst amount, the reaction temperature and the reaction time. The results are shown together in Table 3.

TABLE 3

| | 240fa | Catalyst | Catalyst amount | Reaction temp. (° C.) | Reaction time (h) | GC analysis result (FID %) 240fa | 1230za | others | Conversion (%) | Selectivity (%) |
|---|---|---|---|---|---|---|---|---|---|---|
| Example 3-1 | 50.02 g (0.23 mol) | FeCl$_3$ | 0.93 g (2.5 mol %) | 80 | 4 | 2.8 | 92.8 | 4.4 | 97.1 | 97.2 |
| Example 3-2 | 50.01 g (0.23 mol) | FeCl$_3$ | 0.38 g (1.0 mol %) | 80 | 4 | 3.5 | 92.3 | 4.2 | 96.4 | 97.3 |
| Example 3-3 | 50.02 g (0.23 mol) | AlCl$_3$ | 0.42 g (1.4 mol %) | 80 | 0.5 | 2.8 | 93.0 | 4.2 | 97.2 | 97.4 |
| Example 3-4 | 50.01 g (0.23 mol) | AlCl$_3$ | 0.42 g (1.4 mol %) | 50 | 5 | 3.7 | 91.0 | 5.3 | 96.2 | 96.2 |
| Example 3-5 | 50.00 g (0.23 mol) | FeCl$_3$ | 0.92 g (2.5 mol %) | 50 | 24 | 15.6 | 80.5 | 3.9 | 84.1 | 97.3 |
| Example 3-6 | 50.02 g (0.23 mol) | FeCl$_3$ | 0.38 g (1.0 mol %) | 100 | 1.5 | 0.2 | 84.6 | 15.2 | 99.8 | 86.2 |

It is understood from Table 3 that, in the case of using ferric chloride as the Lewis acid catalyst and in the case of conducting the reaction at around 80° C. (Example 3-1 and Example 3-2), well balanced results have been obtained in terms of both reaction rate and selectivity. On the contrary, in the case of conducting the reaction at 50° C. (Example 3-5), although selectivity was high, the reaction rate lowered such that conversion was limited to around 84% even in 24 hours. On the other hand, in the case of conducting the reaction at 100° C., the reaction rate is high, and the target has been produced at a high yield. However, the by-production of tar-like impurities has been somewhat found, and selectivity on the gas chromatograph has also been lowered.

On the other hand, in the case of using aluminum chloride as the Lewis acid catalyst, well balanced results have been obtained in terms of both reaction rate and selectivity at 50° C., which is somewhat lower than that of ferric chloride.

Reference Example 1

Chlorination of 1,1,3,3-Tetrachloropropene (1230za) in Liquid Phase in the Absence of Catalyst A 100-mL three-necked flask equipped with a ball filter, a thermometer, a Dimroth condenser that allows tap water to flow therethrough, and a stirrer was charged with 39.38 g (0.22 mol) of 1,1,3,3-tetrachloropropene (1230za) having a purity of 98.2 FID %, and then stirring was started. It was connected by using a PFA tube at an upper part of the Dimroth condenser to an empty trap of a 500-mL PFA container and then a 500-mL PFA container charged with 250 g of sodium hydroxide aqueous solution having a concentration of 25 weight %. The flask was heated to 50° C., and 15.87 g (0.22 mol) of chlorine was introduced through the ball filter by spending 127 minutes.

It was found by gas chromatography of the reaction liquid immediately after the introduction of chlorine that 1,1,3,3-tetrachloropropene (1230za) was 21.9 FID % and that 1,1,1,2,3,3-hexachloropropane (230da) was 75.1 FID % (Table 4). In this Reference Example 1, the reaction of the second step was conducted in liquid phase under a condition of no catalyst. The reaction has progressed smoothly, and the target has been obtained. However, at the same temperature, as compared with an experiment (the after-mentioned Example 4-1) conducted by using a Lewis acid catalyst, it is understood that the reaction conversion is low and a longer time is necessary until completing the reaction.

Example 4-1

Second Step (Chlorination of 1,1,3,3-Tetrachloropropene (1230za) in Liquid Phase in the Presence of Lewis Acid Catalyst)

A 100-mL three-necked flask equipped with a ball filter, a thermometer, a Dimroth condenser that allows tap water to flow therethrough, and a stirrer was charged with 41.72 g (0.23 mol) of 1,1,3,3-tetrachloropropene (1230za) having a purity of 98.2 FID % and 0.9 g (0.006 mol) of ferric chloride, and then stirring was started. It was connected by using a PFA tube at an upper part of the Dimroth condenser to an empty trap of a 500-mL PFA container and then a 500-mL PFA container charged with 250 g of sodium hydroxide aqueous solution having a concentration of 25 weight %. Herein, the unreacted chlorine gas passing through the reactor was trapped.

The flask was heated to 50° C., and 16.78 g (0.24 mol) of chlorine was introduced through the ball filter by spending 107 minutes. It was found by gas chromatography of the reaction liquid immediately after the introduction of chlorine that 1,1,3,3-tetrachloropropene (1230za) was 1.2 FID % and that 1,1,1,2,3,3-hexachloropropane (230da) was 95.0 FID % (Table 4). Although conversion of Reference Example 1 with no catalyst was 77.7%, conversion was improved to 98.8% by adding the Lewis acid catalyst, and selectivity was maintained at a high level of 97.9% (see Table 4).

Examples 4-2 to 4-4

Second Step

The reaction was conducted by the same procedure as that of Example 4-1, while modifying the conditions such as reaction temperature. The results are shown in Table 4.

TABLE 4

| | 1230za amount | Catalyst | Catalyst amount | Cl intr. amount intr. rate (g/min) | Reaction temp. (° C.) | GC analysis result (FID %) | | | Conversion (%) | Selectivity (%) |
|---|---|---|---|---|---|---|---|---|---|---|
| | | | | | | 1230za | 230da | others | | |
| Ref. Ex. 1 | 39.38 g (0.22 mol) | None | — | 15.87 g (0.22 mol) 0.12 | 50 | 21.9 | 75.1 | 3.0 | 77.7 | 98.4 |
| Ex. 4-1 | 41.72 g (0.23 mol) | $FeCl_3$ | 0.90 g (2.4 mol %) | 16.78 g (0.24 mol) 0.16 | 50 | 1.2 | 95.0 | 3.9 | 98.8 | 97.9 |
| Ex. 4-2 | 41.08 g (0.23 mol) | $FeCl_3$ | 0.91 g (2.5 mol %) | 16.54 g (0.23 mol) 0.14 | 30 | 2.6 | 94.1 | 3.3 | 97.3 | 98.4 |
| Ex. 4-3 | 41.64 g (0.23 mol) | $FeCl_3$ | 0.90 g (2.4 mol %) | 16.75 g (0.24 mol) 0.14 | 80 | 3.6 | 87.7 | 8.7 | 96.3 | 92.7 |
| Ex. 4-4 | 41.17 g (0.23 mol) | $FeCl_3$ | 0.90 g (2.4 mol %) | 16.73 g (0.24 mol) 0.13 | 100 | 1.0 | 83.1 | 16.0 | 99.0 | 85.4 |

As is clear from Table 4, it is understood that, if the reaction of the second step is conducted in liquid phase in the presence of ferric chloride as the Lewis acid catalyst, the target reaction progresses with a sufficient rate until close to the end point at a temperature around 50° C. or lower. This is in contrast with [Reference Example 1] in which the same reaction resulted in 78% in conversion at 50° C. under no catalyst. That is, it became possible to more efficiently conduct the reaction of the second step than before.

Example 5-1

Third Step (Dehydrochlorination of 1,1,1,2,3,3-Hexachloropropane (230da))

A 100-mL three-necked flask equipped with a ball filter, a thermometer, a Dimroth condenser that allows tap water to flow therethrough, and a stirrer was charged with 58.62 g (0.23 mol) of 1,1,1,2,3,3-hexachloropropane (230da) having a purity of 96.2 FID % and 0.9 g (0.006 mol) of ferric chloride, and then stirring was started. It was connected by using a PFA tube at an upper part of the Dimroth condenser to an empty trap of a 500-mL PFA container and then a 500-mL PFA container charged with 250 g of sodium hydroxide aqueous solution having a concentration of 25 weight %. Herein, hydrogen chloride gas produced as a by-product was trapped.

While nitrogen was introduced through the ball filter at a flow rate of 5 mL/minute, the flask was heated to 130° C. in an oil bath. The reaction was conducted for 2 hours, and at that time it was analyzed by gas chromatography. With this, 1,1,1,2,3,3-hexachloropropane (230da) was 1.3 FID %, 1,1,2,3,3-pentachloropropene (1220xa) was 93.1 FID %, and other impurities were 5.6 FID % (see Table 5).

Example 5-2

Third Step

The results obtained by conducting the reaction by the same procedure of Example 5-1, while modifying the catalyst and the reaction temperature, are similarly shown in Table 5.

TABLE 5

| | 230da amount | Catalyst | Catalyst amount | Reaction temp. (° C.) | Reaction time (h) | GC analysis result (FID %) | | | Conversion (%) | Selectivity (%) |
|---|---|---|---|---|---|---|---|---|---|---|
| | | | | | | 230da | 1220xa | others | | |
| Example 5-1 | 58.62 g (0.23 mol) | $FeCl_3$ | 0.90 g (2.4 mol) | 130 | 2 | 1.3 | 93.1 | 5.6 | 98.6 | 98.1 |
| Example 5-2 | 50.02 g (0.23 mol) | $AlCl_3$ | 0.42 g (1.4 mol) | 80 | 1 | 1.5 | 92.8 | 5.8 | 98.4 | 97.9 |

Example 6-a

One-Pot, Three Steps Reaction (First Step)

A 200-mL three-necked flask equipped with a ball filter, a thermometer, a Dimroth condenser that allows tap water to flow therethrough, and a stirrer was charged with 100.01 g (0.45 mol) of 1,1,1,3,3-pentachloropropane (240fa) having a purity of 98.1 FID % and 0.91 g (0.006 mol) of ferric chloride, and then stirring was started. It was connected by using a PFA tube at an upper part of the Dimroth condenser to an empty trap and then a 500-mL PFA container charged with 250 g of sodium hydroxide aqueous solution having a concentration of 25 weight %. While nitrogen was introduced through the ball filter at a flow rate of 5 mL/minute, the flask was heated to 80° C. in an oil bath. The reaction was conducted for 4.5 hours, and it was analyzed by gas chromatography. With this, 1,1,1,3,3-pentachloropropane (240fa) was 2.8 FID %, and 1,1,3,3-tetrachloropropene (1230za) was 92.7 FID %. The target 1,1,3,3-tetrachloropropene (1230za) was produced with a reaction conversion of 96.9% and a selectivity of 95.7%.

Example 6-b

One-Pot, Three-Steps Reaction (Second Step)

After terminating Example 6-a, the inside temperature of the three-necked flask was lowered to 30° C., and then the reaction mixture was heated to 45° C. by the oil bath. (To start the second step, neither a purification of the reaction mixture of the first step nor a supplementary addition of the Lewis acid catalyst was conducted.) Through ball filter, 32.52 g (0.46 mol) of chlorine was introduced at a flow rate of about 0.2 g/minute by spending 170 minutes. It was found by gas chromatography of the reaction liquid immediately after terminating the introduction that 1,1,3,3-tetrachloropropene (1230za) was 0.2 FID %, and 1,1,1,2,3,3-hexachloropropane (230da) was 93.6 FID %. In was found that the target 1,1,1,2,3,3-hexachloropropane (230da) was produced with a conversion of 99.7% and a selectivity of 93.8%.

Example 6-c

One-Pot, Three Steps Reaction (Third Step)

After terminating Example 6-b, while neither purification nor catalyst supplementation was conducted in particular, nitrogen was introduced through the ball filter at a flow rate of 5 mL/min, and it was adjusted to 120° C. by the oil bath. At this temperature, the reaction was conducted for 2 hours. At this time, it was found by gas chromatography that 1,1,1,2,3,3-hexachloropropane (230da) was 1.8 FID %, and 1,1,2,3,3-pentachloropropene (1220xa) was 93.7 FID %. It was found that the target 1,1,2,3,3-pentachloropropene (1220xa) was produced with a reaction conversion of 98.1% and a selectivity of 95.6%. The flask was cooled with water, and 38.9 g of concentrated hydrochloric acid was added to dissolve solid matter in the flask. From the separated two layers, the lower organic layer was recovered. The organic matter was washed with 53 g of clean water and then with 50 g of saturated sodium hydrogencarbonate, thereby recovering 91.18 g of the organic matter. It was found by gas chromatography to have a purity of 1,1,2,3,3-pentachloropropene (1220xa) of 93.9 FID %, and purity-reduced yield was 88%.

In this way, through Examples 6-a to 6-c, it was found that 1,1,2,3,3-pentachloropropene (1220xa) can be obtained with a good yield by conducting the one-pot, multistep reaction using the same catalyst.

The invention claimed is:

1. A method for producing 1,2-dichloro-3,3,3-trifluoropropene by fluorinating 1,1,2,3,3-pentachloropropene by a reaction with a fluorinating agent, wherein hydrogen fluoride is used as the fluorinating agent, and the reaction is conducted in a liquid phase.

2. The method according to claim 1, wherein usage of the hydrogen fluoride is 3 to 40 mol relative to 1 mol of 1,1,2,3,3-pentachloropropene.

3. The method according to claim 1, wherein the reaction is conducted at 100 to 200° C.

4. The method according to claim 1, wherein the reaction is conducted at 140 to 180° C.

5. The method according to claim 1, wherein the reaction is conducted in the absence or presence of catalyst.

6. The method according to claim 1, wherein the reaction is conducted in the absence of solvent.

7. The method according to claim 1, wherein 1,2,3-trichloro-3,3-difluoropropene, together with 1,2-dichloro-3,3,3-trifluoropropene, is formed by the reaction.

8. The method according to claim 7, wherein 1,2,3-trichloro-3,3-difluoropropene is separated and then is used in the reaction as a raw material for producing 1,2-dichloro-3,3,3-trifluoropropene.

9. The method according to claim 1, further comprising the step of purifying 1,2-dichloro-3,3,3-trifluoropropene.

10. The method according to claim 1, further comprising the step of dehydrochlorinating 1,1,1,2,3,3-hexachloropropane in a liquid phase in the presence of a Lewis acid catalyst to obtain the 1,1,2,3,3-pentachloropropene.

11. The method according to claim 10, wherein the Lewis acid catalyst to be used in the dehydrochlorination of 1,1,1,2,3,3-hexachloropropane comprises a halide of a metal that is at least one selected from the group consisting of aluminum, vanadium, chromium, manganese, iron, cobalt, nickel, copper, zirconium, niobium, molybdenum, ruthenium, rhodium, palladium, silver, tin, antimony, tantalum, and tungsten.

12. The method according to claim 10, further comprising the step of chlorinating 1,1,3,3-tetrachloropropene in a liquid phase in the presence of a Lewis acid catalyst to obtain the 1,1,1,2,3,3-hexachloropropane.

13. The method according to claim 12, further comprising the step of dehydrochlorinating 1,1,1,3,3-pentachloropropane in a liquid phase in the presence of a Lewis acid catalyst to obtain the 1,1,3,3-tetrachloropropene.

14. The method according to claim 13, wherein, when conducting the dehydrochlorination of 1,1,1,3,3-pentachloropropane as a first step, the chlorination of 1,1,3,3-tetrachloropropene as a second step and the dehydrochlorination of 1,1,1,2,3,3-hexachloropropane as a third step in this order, the Lewis acid catalyst used in the first step is reused in the second and third steps as the Lewis acids of the second and third steps.

15. A method for producing both 1,2-dichloro-3,3,3-trifluoropropene and 1,2,3-trichloro-3,3-difluoropropene by reacting 1,1,2,3,3-pentachloropropene with hydrogen fluoride, and the reaction is conducted in a liquid phase.

16. The method according to claim 15, wherein the reaction is conducted in the presence or absence of a catalyst.

17. The method according to claim 15, further comprising the step of separating 1,2-dichloro-3,3,3-trifluoropropene and 1,2,3-trichloro-3,3-difluoropropene.

18. A method for producing 1,2-dichloro-3,3,3-trifluoropropene by fluorinating 1,1,2,3,3-pentachloropropene by a reaction with a fluorinating agent, wherein hydrogen fluoride is used as the fluorinating agent, and the reaction is conducted in a gas phase and in the absence of catalyst.

19. The method according to claim 18, wherein the reaction is conducted at 160 to 600° C.

20. The method according to claim 18, wherein the reaction is conducted in the presence of at least one selected from the group consisting of chlorine, oxygen and air.

21. The method according to claim 18, wherein 1,2,3-trichloro-3,3-difluoropropene is further produced and wherein 1,2,3-trichloro-3,3-difluoropropene is separated and then is used in the reaction as a raw material for producing 1,2-dichloro-3,3,3-trifluoropropene.

22. A method for producing both 1,2-dichloro-3,3,3-trifluoropropene and 1,2,3-trichloro-3,3-difluoropropene by fluorinating 1,1,2,3,3-pentachloropropene by a reaction with a fluorinating agent, wherein hydrogen fluoride is used as the fluorinating agent, the reaction is conducted in a gas phase, and 1,2,3-trichloro-3,3-difluoropropene is separated and then is used in the reaction as a raw material for producing 1,2-dichloro-3,3,3-trifluoropropene.

23. The method according to claim 22, wherein the reaction is conducted at 160 to 600° C.

24. The method according to claim 22, wherein the reaction is conducted in the absence or presence of catalyst.

25. The method according to claim 22, wherein the reaction is conducted by using a catalyst that is a metal oxide, a metal fluoride or a metal compound-supported catalyst, and wherein the catalyst is optionally subjected to a fluorination treatment to be used in the reaction.

26. The method according to claim 22, wherein the reaction is conducted in the presence of at least one selected from the group consisting of chlorine, oxygen and air.

* * * * *